US012648914B2

(12) United States Patent
Helliwell et al.

(10) Patent No.: US 12,648,914 B2
(45) Date of Patent: **\*Jun. 9, 2026**

(54) INJECTABLE SUSTAINED RELEASE COMPOSITION AND METHOD OF USING THE SAME FOR TREATING INFLAMMATION IN JOINTS AND PAIN ASSOCIATED THEREWITH

(71) Applicant: Eupraxia Pharmaceuticals USA LLC, Victoria (CA)

(72) Inventors: James A. Helliwell, Victoria (CA); Amanda M. Malone, Victoria (CA); Thomas J. Smith, Santa Monica, CA (US); Marc M. Baum, Pasadena, CA (US)

(73) Assignee: Eupraxia Pharmaceuticals USA LLC, Vancouver (CA)

( * ) Notice: Subject to any disclaimer, the term of this patent is extended or adjusted under 35 U.S.C. 154(b) by 699 days.

This patent is subject to a terminal disclaimer.

(21) Appl. No.: 17/457,248

(22) Filed: Dec. 1, 2021

(65) Prior Publication Data

US 2022/0087943 A1     Mar. 24, 2022

Related U.S. Application Data

(60) Continuation of application No. 15/975,577, filed on May 9, 2018, now Pat. No. 11,219,604, which is a (Continued)

(51) Int. Cl.
*A61K 9/50*     (2006.01)
*A61K 9/00*     (2006.01)
(Continued)

(52) U.S. Cl.
CPC .......... *A61K 9/5026* (2013.01); *A61K 9/0024* (2013.01); *A61K 31/56* (2013.01); *A61K 31/58* (2013.01)

(58) Field of Classification Search
CPC .... A61K 9/5026; A61K 9/0024; A61K 31/56; A61K 31/58; A61P 7/10; A61P 17/02;
(Continued)

(56) References Cited

U.S. PATENT DOCUMENTS

| 2,515,898 A | 7/1950 | Rhodehamel, Jr. |
| 2,627,491 A | 2/1953 | Lester et al. |

(Continued)

FOREIGN PATENT DOCUMENTS

| CN | 1679515 A | 10/2005 |
| CN | 102070895 A | 5/2011 |

(Continued)

OTHER PUBLICATIONS

Office Action, dated Oct. 22, 2020, for Indian Application No. 201817016199, 7 pages. (w/ English Translation).

(Continued)

*Primary Examiner* — Sahana S Kaup
*Assistant Examiner* — Lucy M Tien
(74) *Attorney, Agent, or Firm* — Seed Intellectual Property Law Group LLP

(57)     ABSTRACT

Described herein are injectable corticosteroid-loaded microparticles, pharmaceutical composition thereof and methods for reducing inflammation or pain in a body compartment such as a joint, an epidural space, a vitreous body of an eye, a surgically created space, or a space adjacent to an implant.

6 Claims, 8 Drawing Sheets

Related U.S. Application Data division of application No. 14/222,082, filed on Mar. 21, 2014, now Pat. No. 9,987,233.

(60) Provisional application No. 61/804,185, filed on Mar. 21, 2013.

(51) Int. Cl.
A61K 31/56 (2006.01)
A61K 31/58 (2006.01)

(58) Field of Classification Search
CPC .......... A61P 19/02; A61P 25/00; A61P 25/04;
A61P 27/02; A61P 29/00
USPC ........................................................ 424/497
See application file for complete search history.

(56) References Cited

U.S. PATENT DOCUMENTS

| | | | |
|---|---|---|---|
| 3,867,519 A | 2/1975 | Michaels | |
| 3,993,073 A | 11/1976 | Zaffaroni | |
| 4,105,776 A | 8/1978 | Ondetti et al. | |
| 4,231,938 A | 11/1980 | Monaghan et al. | |
| 4,244,836 A | 1/1981 | Frensch et al. | |
| 4,316,906 A | 2/1982 | Ondetti et al. | |
| 4,337,201 A | 6/1982 | Petrillo, Jr. | |
| 4,344,949 A | 8/1982 | Hoefle et al. | |
| 4,346,227 A | 8/1982 | Terahara et al. | |
| 4,374,829 A | 2/1983 | Harris et al. | |
| 4,410,520 A | 10/1983 | Watthey | |
| 4,427,649 A | 1/1984 | Dingle et al. | |
| 4,439,196 A | 3/1984 | Higuchi | |
| 4,444,784 A | 4/1984 | Hoffman et al. | |
| 4,452,025 A | 6/1984 | Lew | |
| 4,508,729 A | 4/1985 | Vincent et al. | |
| 4,512,924 A | 4/1985 | Attwood et al. | |
| 4,530,840 A | 7/1985 | Tice et al. | |
| 4,542,025 A | 9/1985 | Tice et al. | |
| 4,568,559 A | 2/1986 | Nuwayser et al. | |
| 4,587,258 A | 5/1986 | Gold et al. | |
| 4,623,588 A | 11/1986 | Nuwayser et al. | |
| 4,652,441 A | 3/1987 | Okada et al. | |
| 4,675,196 A | 6/1987 | Villa et al. | |
| 4,739,073 A | 4/1988 | Kathawala | |
| 4,757,128 A | 7/1988 | Domb et al. | |
| 4,789,724 A | 12/1988 | Domb et al. | |
| 4,857,311 A | 8/1989 | Domb et al. | |
| 4,888,176 A | 12/1989 | Langer et al. | |
| 4,897,402 A | 1/1990 | Duggan et al. | |
| 4,904,646 A | 2/1990 | Karanewsky et al. | |
| 4,906,624 A | 3/1990 | Chucholowski et al. | |
| 4,906,657 A | 3/1990 | Roth | |
| 4,920,109 A | 4/1990 | Onishi et al. | |
| 4,923,861 A | 5/1990 | Picard et al. | |
| 4,929,620 A | 5/1990 | Chucholowski et al. | |
| 4,939,143 A | 7/1990 | Regan et al. | |
| 4,940,727 A | 7/1990 | Inamine et al. | |
| 4,940,800 A | 7/1990 | Bertolini et al. | |
| 4,946,860 A | 8/1990 | Morris et al. | |
| 4,946,864 A | 8/1990 | Prugh et al. | |
| 4,950,675 A | 8/1990 | Chucholowski | |
| 4,957,940 A | 9/1990 | Roth | |
| 4,963,538 A | 10/1990 | Duggan et al. | |
| 4,968,693 A | 11/1990 | Joshua et al. | |
| 4,970,231 A | 11/1990 | Lee et al. | |
| 4,992,429 A | 2/1991 | Ullrich et al. | |
| 4,994,281 A | 2/1991 | Muranishi et al. | |
| 4,994,494 A | 2/1991 | Regan et al. | |
| 4,996,234 A | 2/1991 | Regan et al. | |
| 4,997,837 A | 3/1991 | Chucholowski et al. | |
| 5,001,128 A | 3/1991 | Neuenschwander et al. | |
| 5,001,144 A | 3/1991 | Regan et al. | |
| 5,017,716 A | 5/1991 | Karanewsky et al. | |
| 5,021,453 A | 6/1991 | Joshua et al. | |
| 5,025,000 A | 6/1991 | Karanewsky | |
| 5,081,136 A | 1/1992 | Bertolini et al. | |
| 5,091,185 A | 2/1992 | Castillo et al. | |
| 5,091,378 A | 2/1992 | Karanewsky et al. | |
| 5,091,386 A | 2/1992 | Kesseler et al. | |
| 5,098,931 A | 3/1992 | Duggan et al. | |
| 5,102,911 A | 4/1992 | Lee et al. | |
| 5,112,857 A | 5/1992 | Vickers | |
| 5,116,870 A | 5/1992 | Smith et al. | |
| 5,130,306 A | 7/1992 | Duggan et al. | |
| 5,132,312 A | 7/1992 | Regan et al. | |
| 5,133,947 A | 7/1992 | Stambaugh et al. | |
| 5,133,974 A | 7/1992 | Paradissis et al. | |
| 5,135,935 A | 8/1992 | Alberts et al. | |
| 5,166,171 A | 11/1992 | Jendralla et al. | |
| 5,182,298 A | 1/1993 | Helms et al. | |
| 5,196,440 A | 3/1993 | Bertolini et al. | |
| 5,202,327 A | 4/1993 | Robl | |
| 5,250,435 A | 10/1993 | Cover et al. | |
| 5,256,689 A | 10/1993 | Chiang | |
| 5,260,332 A | 11/1993 | Dufresne | |
| 5,262,435 A | 11/1993 | Joshua et al. | |
| 5,271,946 A | 12/1993 | Hettche | |
| 5,273,995 A | 12/1993 | Roth | |
| 5,276,021 A | 1/1994 | Karanewsky et al. | |
| 5,283,256 A | 2/1994 | Dufresne et al. | |
| 5,286,497 A | 2/1994 | Hendrickson et al. | |
| 5,286,895 A | 2/1994 | Harris et al. | |
| 5,302,604 A | 4/1994 | Byrne et al. | |
| 5,310,572 A | 5/1994 | Woodard et al. | |
| 5,317,031 A | 5/1994 | MacConnell et al. | |
| 5,356,896 A | 10/1994 | Kabadi et al. | |
| 5,369,125 A | 11/1994 | Berger et al. | |
| 5,378,475 A | 1/1995 | Smith et al. | |
| 5,385,932 A | 1/1995 | Vickers | |
| 5,567,473 A | 10/1996 | Lacz et al. | |
| 5,618,563 A | 4/1997 | Berde et al. | |
| 5,622,985 A | 4/1997 | Olukotun et al. | |
| 5,639,480 A | 6/1997 | Bodmer et al. | |
| 5,651,990 A | 7/1997 | Takada et al. | |
| 5,654,009 A | 8/1997 | Hata et al. | |
| 5,700,485 A | 12/1997 | Berde et al. | |
| 5,753,234 A | 5/1998 | Lee et al. | |
| 5,922,340 A | 7/1999 | Berde et al. | |
| 6,046,187 A | 4/2000 | Berde et al. | |
| 6,120,787 A | 9/2000 | Gustafsson et al. | |
| 6,214,387 B1 | 4/2001 | Berde et al. | |
| 6,238,702 B1 | 5/2001 | Berde et al. | |
| 6,326,020 B1 | 12/2001 | Kohane et al. | |
| 6,426,339 B1 | 7/2002 | Berde et al. | |
| 6,544,646 B2 | 4/2003 | Vaghefi et al. | |
| 6,936,270 B2 | 8/2005 | Watson et al. | |
| 7,063,862 B2 | 6/2006 | Lin et al. | |
| 8,263,108 B2 | 9/2012 | Gibson et al. | |
| 8,765,725 B2 | 7/2014 | Cavanagh et al. | |
| 9,957,233 B1 | 5/2018 | Xi | |
| 2002/0114844 A1 | 8/2002 | Hanna et al. | |
| 2003/0152637 A1 | 8/2003 | Chasin et al. | |
| 2004/0191326 A1 | 9/2004 | Reo et al. | |
| 2004/0208833 A1 | 10/2004 | Hovey et al. | |
| 2005/0069591 A1 | 3/2005 | Bernstein et al. | |
| 2007/0003619 A1 | 1/2007 | Smith | |
| 2007/0026527 A1 | 2/2007 | Delacourte et al. | |
| 2007/0218139 A1* | 9/2007 | Smith .................. A61K 9/5084 424/489 |
| 2008/0044476 A1 | 2/2008 | Lyons et al. | |
| 2008/0317805 A1 | 12/2008 | McKay et al. | |
| 2009/0082321 A1 | 3/2009 | Edelman et al. | |
| 2009/0264472 A1 | 10/2009 | Wohabrebbi et al. | |
| 2010/0196482 A1 | 8/2010 | Radovic-Moreno et al. | |
| 2011/0081420 A1 | 4/2011 | Barrows | |
| 2011/0238036 A1 | 9/2011 | Ashton | |
| 2012/0282298 A1 | 11/2012 | Bodick et al. | |
| 2013/0052264 A1 | 2/2013 | Chung et al. | |
| 2013/0122085 A1 | 5/2013 | Dalton et al. | |
| 2013/0316006 A1 | 11/2013 | Popov et al. | |
| 2013/0316009 A1 | 11/2013 | Popov | |

(56) References Cited

U.S. PATENT DOCUMENTS

| 2013/0337073 A1 | 12/2013 | Oshima et al. |
| 2015/0044271 A1 | 2/2015 | Slattery et al. |

FOREIGN PATENT DOCUMENTS

| EP | 2113013 A2 | 11/2009 |
| EP | 2976062 A1 | 1/2016 |
| GB | 2 241 889 A | 9/1991 |
| JP | 61191609 | 11/1986 |
| JP | 1311024 | 12/1989 |
| JP | 2006521287 A | 9/2006 |
| JP | 2006523613 A | 10/2006 |
| JP | 4230210 B2 | 2/2009 |
| JP | 2010111592 A | 5/2010 |
| JP | 2010540447 A | 12/2010 |
| JP | 2013535489 A | 9/2013 |
| RU | 2262355 C1 | 10/2005 |
| WO | 9813027 A1 | 4/1998 |
| WO | 0228371 A1 | 4/2002 |
| WO | 2004058222 A1 | 7/2004 |
| WO | 2004058223 A1 | 7/2004 |
| WO | 2005009604 A1 | 2/2005 |
| WO | 2008048770 A1 | 4/2008 |
| WO | 2008103123 A2 | 8/2008 |
| WO | 2008119033 A1 | 10/2008 |
| WO | 2009001697 A2 | 12/2008 |
| WO | 2009039262 A2 | 3/2009 |
| WO | 2010007446 A1 | 1/2010 |
| WO | 2010017265 A2 | 2/2010 |
| WO | 2010052896 A1 | 5/2010 |
| WO | 2012019009 A1 | 2/2012 |
| WO | 2013130619 A1 | 9/2013 |
| WO | 2014153541 A1 | 9/2014 |
| WO | 2016044799 A1 | 3/2016 |

OTHER PUBLICATIONS

Soulas et al., "Drug Release from Poly(dimethylsiloxane)-Based Matrices: Observed and Predicted Stabilization of the Release Rate by Three-Layer Devices," Industrial & Engineering Chemistry Research 51:7126-7136, 2012.
English Translation of Office Action, mailed Jun. 10, 2019, for IL Application No. 241718, 4 pages.
Office Action, mailed Oct. 10, 2019, for CA Application No. 2,907,765, 3 pages.
Rabinow et al., "Intra-articular (IA) Ropivacaine Microparticle Suspensions Reduce Pain, Inflammation, Cytokine, and Substance P Levels Significantly More than Oral or IA Celecoxib in a Rat Model of Arthritis," Inflammation 38(1):40-60, 2015.
Supplementary European Search Report dated Apr. 14, 2011 for corresponding European Patent Application No. 03800247.3.
Adams et al., Depot fluphenazine for schizophrenia, Cochrane Database Syst. Rev. 2000.
Fleckenstein, History of calcium antagonists, Cir. Res./Suppl. 1, 1983, pp. 1-3-1-16, 52(2).
Mollmann et al., Clinical and pharmacologic aspects of various betamethasone crystalline suspensions, fortschr. Med., 1977, pp. 972-978, 95(14).
O'Keefe et al., Should an angiotensin-converting enzyme inhibitor be standard therapy for patients with atherosclerotic disease?, J. Am. Coll. Cardiol., pp. 1-8, 37(1).
Table 16-1, Remington: The Science and Practice of Pharmacy, 2000, p. 209, 20th Ed.
Arnsten et al. "Antiretroviral Therapy Adherence and Viral Suppression in HIV-Infected Drug Users: Comparison of Self-Report and Electronic Monitoring," Clinical Infectious Diseases 33:1417-1423, Oct. 15, 2001.
Bartlett et al., "Management of Anthrax," Clinical Infectious Diseases 35:851-858, Oct. 1, 2002.

Blauw et al., "Stroke, Statins, and Cholesterol: A Meta-Analysis of Randomized, Placebo-Controlled Double-Blind Trials With HMG-CoA Reductase Inhibitors," Stroke 28:946-950, 1997.
Burch et al., "Current Indications for ACE Inhibitors and HOPE for the Future," The American Journal of Managed Care 8:478-490, 2002.
Byron et al., "Effects of Heat Treatment on the Permeability of Polyvinyl Alcohol Films to a Hydrophilic Solute," Journal of Pharmaceutical Sciences 76(1):65-67, Jan. 1987.
Cadorniga et al., "In vitro evaluation of the dissolution rate of crystalline suspensions destined to intramuscular administration," European Journal of Drug Metabolism and Pharmacokinetics S3:379-384, 1991.
Cushenberry et al., "Potential Use of HMG-COA Reductase Inhibitors for Osteoporosis," The Annals of Phamacotherapy 36:671-678, 2002.
David et al., "Depot fluphenazine decanoate and enanthate for schizophrenia (Review)," The Cochrane Collaboration, 2006, 137 pages.
Dechend et al., "Modulating Angiotensin II-Induced Inflammation by HMG Co-A Reductase Inhibition," The American Journal of Hypertension 14:55S-61S, 2001.
Endres et al., "Stroke protection by 3-hydroxy-3-methylglutaryl (HMG)-CoA reductase inhibitors mediated by endothelial nitric oxide synthase," Proc. Natl. Acad. Sci. USA 95:8880-8885, Jul. 1998.
Fassbender et al., "Effects of statins on human cerebral cholesterol metabolism and secretion of Alzheimer amyloid peptide," Neurology 59:1257-1258, 2002.
Friedlander et al., "Postexposure Prophylaxis against Experimental Inhalation Anthrax," The Journal of Infectious Diseases 167:1239-1242, 1993.
Gennaro et al. (eds.), Remington: The Science and Practice of Pharmacy, 19th ed., Williams & Wilkins, Baltimore, Maryland, USA, 1995, p. 963. (1 page).
Gennaro et al. (eds.), Remington: The Science and Practice of Pharmacy, 20th ed., Lippincott Williams & Wilkins, Baltimore, Maryland, USA, 2000, p. 209. (1 page).
Gennaro et al. (eds.), Remington: The Science and Practice of Pharmacy, 20th ed., Lippincott Williams & Wilkins, Baltimore, Maryland, USA, 2000, p. 1371. (3 pages).
Gharabawi et al., "Enhanced psychiatric and neurological outcomes in chronically psychotic patients treated for a year with long-acting, injectable risperidone," Annual Meeting American College of Neuropsychopharmacology, San Juan, PR, 2002, 1 page.
Houghton, "Angiotensin II Receptor Antagonists in Chronic Heart Failure," Drugs 62(10):1433-1440, 2002.
Jefferds et al., "Adherence to Antimicrobial Inhalational Anthrax Prophylaxix among Postal Workers, Washington, D.C., 2001," Emerging Infectious Diseases 8(10):1138-1144, 2002.
Kaplan et al., "Pharmacokinetics of benzathine penicillin G: Serum levels during the 28 days after intramuscular injection of 1,200,000 units," J. Pediatr 115:146-150, 1989.
McCall et al., "Calcium entry blocking drugs: mechanisms of action, experimental studies and clinical uses," Curr. Probl. Cardiol. 10(8):1-80, 1985.
Mimran et al., "Angiotensin II receptor antagonists and hypertension," Clin. and Exper. Hypertension 21(5&6):847-858, 1999.
Möllmann et al., "Klinisch-pharmakologiche Aspekte unterschiedlicher Betamethason-Kristallsuspensionen," Fortschr. Med. 95(14):972-978, 1977.
O'Keefe et al., "Should an Angiotensin-Converting Enzyme Inhibitor Be Standard Therapy for Patients With Atherosclerotic Disease?," Journal of the American College of Cardiology 37(1):1-8, 2001.
Perico et al., "Angiotensin II receptor antagonists and treatment of hypertension and renal disease," Curr. Opin. Nephrol. Hypertens. 7:571-578, 1998.
Quraishi et al., "Depot haloperidol decanoate for schizophrenia (Review)," The Cochrane Collaboration, 2006, 37 pages.
Subhaga et al., "Evaluation of an aliphatic polyurethane as a microsphere matrix for sustained theophylline delivery," J. Microencapsulation 12(6):617-625, 1995.

(56)　　　　　References Cited

OTHER PUBLICATIONS

Supplementary European Search Report dated Apr. 21, 2011, for corresponding European Application No. 03800247.3-1219 / 1585500, 3 pages.

Wong et al., "Nonpeptide Angiotensin II Receptor Antagonists. I. Pharmacological Characterization of 2-n-Butyl-4-chloro-1-(2-chlorobenzyl)imidazole-5-acetic acid, sodium salt (S-8307)," The Journal of Pharmacology and Experimental Therapeutics 247(1):1-8, 1988.

Nichols, "Hormones and hormone antagonists," Remington: The Science and Practice of Pharmacy, 20th Edition, Limmer, ed., 2000, p. 1371.

Remington: The Science and Practice of Pharmacy 19th Edition, vol. II, Gennaro, ed., p. 963, 1995.

Remington: The Science and Practice of Pharmacy 20th Edition, Limmer, ed., Table 16-1, p. 209.

"Armstrong-Kropp Development Corporation's Applications", R.P. C., pp. 268-271, 1974.

"Whitehead Institute for Biomedical Research, Max-Planck-Gesellschaft Zur Forderung Der Wissenschaften Ev, Massachusetts Institute of Technology, and University of Massachusetts Medical Center", Intellectual Property Office of New Zealand—Patent Decisions, NZIPOPAT 21, 2009 (9 pages).

Gennaro et al. (eds.), "Hormones and hormone antagonists," Remington: The Science and Practice of Pharmacy, 20th ed., Lippincott Williams & Wilkins, Baltimore, Maryland, USA, 2000, p. 1371. (3 pages).

International Search Report, dated May 25, 2004, for International Application No. PCT/US03/41391. (2 pages).

International Search Report and Written Opinion, dated Dec. 22, 2015, for International Application No. PCT/US15/51072. (7 pages).

International Search Report and Written Opinion, dated Jun. 20, 2014, for International Application No. PCT/US2014/031502. (7 pages).

International Search Report and Written Opinion. dated Jan. 19, 2017, for International Application No. PCT/US2016/059141. (11 pages).

Office Action, dated Jan. 26, 2020, for Australian Application No. 2015317339, 3 pages.

Office Action, dated Aug. 7, 2020, for Brazilian Application No. BR112018008415-8, 7 pages. (w/ English Translation).

Office Action, dated Feb. 6, 2019, for Chilean Application No. 201801098, 19 pages. (w/ English Machine Translation).

Office Action, dated Mar. 22, 2021, for Chinese Application No. 201910668623.9, 9 pages. (w/ English Translation).

Office Action, dated Mar. 4, 2020, for European Application No. 15841849.1, 5 pages.

Office Action, dated Jun. 29, 2020, for Indian Application No. 8857/DELNP/2015, 6 pages. (w/ English Translation).

* cited by examiner

Differential Volume (Average) (2 S.D.)

0.375 μm to 948.3 μM

Volume: 100%
Mean:    119.6 μm
Median: 118.5 μm
S.D.:      41.14 μm
De:        75.26 μm
De:        118.5 μm
De:        172.7 μm PVA_coated_FLUT_-106_+75

Particle Diameter (μm)

Differential Volume (Average) (2 S.D.)

TRIAMCINOLONE 0.375 μm to 948.3 μM

Volume: 100%
Mean:    15.96 μm
Median: 13.12 μm
S.D.:      13.20 μm
De:        1.376 μm
De:        13.12 μm
De:        33.56 μm Particle Diameter (μm)

INJECTABLE SUSTAINED RELEASE COMPOSITION AND METHOD OF USING THE SAME FOR TREATING INFLAMMATION IN JOINTS AND PAIN ASSOCIATED THEREWITH

CROSS-REFERENCE TO RELATED APPLICATIONS

This application is a continuation application of U.S. patent application Ser. No. 15/975,577, filed May 9, 2018, which is a divisional application of U.S. patent application Ser. No. 14/222,082, filed Mar. 21, 2014, now issued U.S. Pat. No. 9,987,233, which claims the benefit under 35 U.S.C. § 119(e) of U.S. Provisional Patent Application No. 61/804,185, filed Mar. 21, 2013. These applications are incorporated herein by reference in their entireties.

BACKGROUND

Technical Field

This disclosure relates to an injectable sustained release composition and a method of delivery of the same to reduce inflammation and to treat pain in joints, including pain caused by inflammatory diseases such as osteoarthritis or rheumatoid arthritis.

Description of the Related Art

Arthritis i.e., inflammation in the joints, consists of more than 100 different conditions which range from relatively mild forms of tendinitis and bursitis to crippling systemic forms, such as rheumatoid arthritis. It includes pain syndromes such as fibromyalgia and arthritis-related disorders, such as systemic lupus erythematosus, that involve every part of the body.

Generally, there are two types of arthritis:

Rheumatoid arthritis ("RA") and related diseases, which are immune-mediated systemic inflammatory joint diseases.

Osteoarthritis ("OA"), which is a degenerative joint disease, the onset of which is typically mediated by previous joint injury or other factors.

The common denominator for all of these arthritic conditions, including RA and OA is joint and musculoskeletal pain. Often this pain is a result of inflammation of the joint lining which is the body's natural response to injury. Such inflammation and pain can prevent the normal use and function of the joint. Pain and disability from arthritis, joint degeneration, and surgery are generally treated by a combination of oral medications or intra-articular injections of steroid compounds designed to reduce inflammation. In addition, other compositions, such as hyaluronic acid products, have been injected to provide visco-supplementation. A distinct benefit of a corticosteroid injection is that the relief of localized inflammation in a particular body area is more rapid and powerful than what can be achieved with traditional anti-inflammatory oral medications, such as aspirin. A single injection also can avoid certain side effects that can accompany multiple doses of oral anti-inflammatory medications, notably irritation of the stomach. Injections can be administered easily in a doctor's office. Other advantages include the rapid onset of the medication's action. Unfortunately, injections also have some systemic side effects or are not effective for extended periods of time.

Short-term complications are uncommon. Long-term risks of corticosteroid injections depend on the dose and frequency of the injections. With higher doses and frequent administration, potential side effects include thinning of the skin, easy bruising, weight gain, puffiness of the face, acne (steroid acne), elevation of blood pressure, cataract formation, thinning of the bones (osteoporosis), and a rare but serious type of damage to the bones of the large joints (avascular necrosis). Furthermore, there is an interdependent feedback mechanism between the hypothalamus, which is responsible for secretion of corticotrophin-releasing factor, the pituitary gland, which is responsible for secretion of adrenocorticotropic hormone, and the adrenal cortex, which secretes cortisol, termed the hypothalamic-pituitary-adrenal (HPA) axis. The HPA axis may be suppressed by the administration of corticosteroids, leading to a variety of unwanted side effects.

Accordingly, there is a medical need to extend the local duration of action of corticosteroids, while reducing the systemic side effects associated with that administration. In addition, there is a need for sustained local treatment of pain and inflammation, such as joint pain, with corticosteroids that results in clinically insignificant or no measurable HPA axis suppression. In addition, there is a medical need to slow, arrest, reverse or otherwise inhibit structural damage to tissues caused by inflammatory diseases such as damage to articular tissues resulting from osteoarthritis or rheumatoid arthritis.

BRIEF SUMMARY

Described herein are pharmaceutical compositions, injectable dosage forms and method of using the same for treating inflammation and/or manage pain in a body compartment, such as a joint space, an epidural space, a vitreous body of an eye, a surgically created space, or a space adjacent to an implant.

One embodiment provides a pharmaceutical composition, comprising: a plurality of microparticles, the microparticle including: (1) a crystalline drug core of more than 70% by weight of the microparticle, the crystalline drug core including one or more crystals of fluticasone or a pharmaceutically acceptable salt or ester thereof; and (2) a polymeric shell encapsulating the crystalline drug core, the polymeric shell being in contact but immiscible with the crystalline drug core, wherein said microparticles when dissolution tested using United States Pharmacopoeia Type II apparatus exhibit a dissolution half-life of 12-20 hours, wherein the dissolution conditions are: 3 milligrams of microparticles in 200 milliliters of dissolution medium of 70% v/v methanol and 30% v/v of water at 25° C.

A further embodiment provides a pharmaceutical composition, comprising: a plurality of microparticles, the microparticle including: (1) a crystalline drug core of more than 70% by weight of the microparticle, the crystalline drug core including one or more crystals of fluticasone or a pharmaceutically acceptable salt or ester thereof; and (2) a polymeric shell encapsulating the crystalline drug core, the polymeric shell being in contact but immiscible with the crystalline drug core, wherein the microparticles are heat treated within a temperature range of 210-230° C. for at least one hour.

Yet another embodiment provides a unit dosage form of a corticosteroid for injecting into a body compartment, comprising: a plurality of microparticles, the microparticle including: (1) a crystalline drug core of more than 70% by weight of the microparticle; and (2) a polymeric shell encapsulating the crystalline drug core, wherein the crystalline drug core includes one or more crystals of a corticosteroid selected from fluticasone, fluticasone furoate, and fluticasone propionate, and the polymeric shell is in contact but immiscible with the crystalline drug core, wherein the unit dosage form is capable of sustained-release of the corticosteroid over a period of 2-12 months while maintaining a minimum therapeutically effective concentration of the corticosteroid within the body compartment.

Yet a further embodiment provides a method of decreasing inflammation or managing pain in a patient in need thereof comprising administering to the patient, via injection to a body compartment, a therapeutically effective amount of a pharmaceutical composition for sustained release of a corticosteroid wherein the pharmaceutical composition comprises a plurality of microparticles and a pharmaceutically acceptable vehicle, the microparticle including: (1) a crystalline drug core of more than 70% by weight of the microparticle; and (2) a polymeric shell encapsulating the crystalline drug core, and wherein the crystalline drug core includes one or more crystals of fluticasone or a pharmaceutically acceptable salt or ester thereof, and the polymeric shell is in contact but immiscible with the crystalline drug core.

A further embodiment provides a method for forming coated microparticles, comprising: providing a crystalline drug core including one or more crystals of a corticosteroid, forming a polymeric shell by coating one or more coats of a polymeric solution having a biodegradable polymer and a solvent; allowing the solvent to dry to provide coated microparticles; and heating the coated microparticles at 210-230° C. for at least one hour.

Yet another embodiment provides a method of decreasing inflammation or managing pain in a patient in need thereof comprising: administering to the patient, via a single injection to a body compartment, a unit dosage form for sustained release of a corticosteroid wherein the unit dosage form comprises a plurality of microparticles and a pharmaceutically acceptable vehicle, wherein the crystalline drug core includes one or more crystals of a corticosteroid selected from fluticasone, fluticasone furoate, and fluticasone propionate, and the polymeric shell is in contact but immiscible with the crystalline drug core, and wherein, following the single injection, the corticosteroid is released over a period of 2-12 months while maintaining a minimum therapeutically effective concentration of the corticosteroid within the body compartment.

The present disclosure further provides a corticosteroid which is administered locally as a sustained release dosage form (with or without an immediate release component) that results in efficacy accompanied by clinically insignificant or no measurable effect on endogenous cortisol production.

The present disclosure further provides a membrane based, diffusion-driven release mechanism with drug particle sizing large enough to allow high drug loading, but small enough to be injected intra-articularly.

The present disclosure further provides a use of an intra-articularly injected, therapeutically effective amount of a pharmaceutical preparation for sustained release of a corticosteroid selected from the group consisting of fluticasone, fluticasone furoate, and fluticasone propionate, comprising a multiplicity of coated microparticles, said coated microparticles having a mean diameter in a range of 50 μm to 400 μm and wherein the microparticles are particles comprised of greater than 70% corticosteroid by weight, to decrease inflammation and to reduce pain in a patient.

As provided herein, corticosteroids ("drug" or "therapeutic agent") are coated with a semi-permeable polymeric shell and injected into the joint. Water then diffuses through the polymer and dissolves the drug core (D) creating a saturated solution inside the membrane (C) and essentially sink conditions outside the particle (c). This concentration gradient drives a constant (zero order) release of drug from the drug particle as long as there is some drug core remaining to maintain a saturated solution. The period of release can be tuned by altering the permeability of the polymer coating.

The present disclosure further relates to the delivery of compositions to reduce inflammation and to treat pain in joints, including pain caused by inflammatory diseases such as osteoarthritis or rheumatoid arthritis and to slow, arrest or reverse structural damage to tissues caused by an inflammatory disease, for example damage to articular and/or peri-articular tissues caused by osteoarthritis or rheumatoid arthritis.

By way of the method of the present disclosure, there is provided a means to reduce morbidity due to arthritis by employing and administering to a patient a long-lasting injectable, intra-articular drug delivery composition. While intra-articular steroids have been a mainstay of treatment for arthritis for more than 50 years, for many patients, multiple steroid injections are necessary with attendant risks and side effects. There is provided herein a platform and method to overcome these side effects via a sustained release delivery method, which can provide pseudo-zero order release, without an initial burst, on the order of months for low solubility steroids. An intra-articular injectable formulation for this use and with these properties has never been described in the literature.

BRIEF DESCRIPTION OF THE SEVERAL VIEWS OF THE DRAWINGS

The following figures set forth embodiments in which like reference numerals denote like parts. Embodiments are illustrated by way of example and not by way of limitation in all of the accompanying figures wherein.

DETAILED DESCRIPTION

Figure 1:
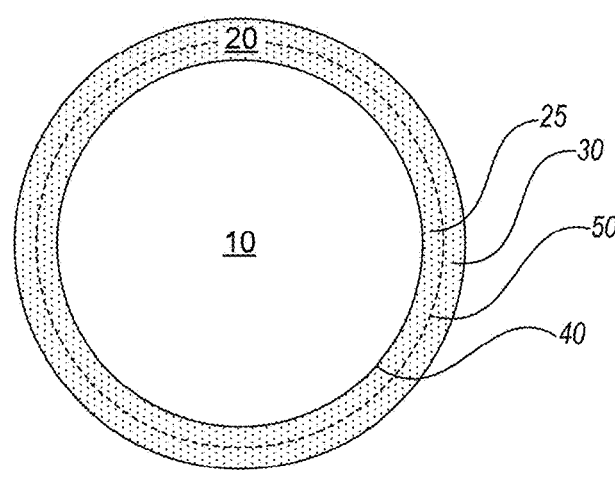
FIG. 1 shows schematically a microparticle of core/shell morphology.

Described herein are pharmaceutical compositions, injectable dosage forms and method of using the same for treating inflammation and/or manage pain in a body compartment, such as a joint space, an epidural space, a vitreous body of an eye, a surgically created space, or a space adjacent to an implant. The pharmaceutical composition includes a plurality of microparticles in core/shell morphology. In particular, the microparticle includes a crystalline drug core of a corticosteroid and a polymeric shell encapsulating the crystalline drug core. As discussed in further detail herein, the injectable microparticles are characterized with high drug-loading, narrow size distribution and a sustained release profile of pseudo zero-order release over a period of 2-12 months within a body compartment, e.g., a joint.

Several studies have confirmed that the efficacy of intra-articular corticosteroids is directly related to their intra-articular residence time. Caldwell J R. Intra-articular corticosteroids. Guide to selection and indications for use. *Drugs* 52(4):507-514, 1996. It has been surprisingly found that when a direct injection of the pharmaceutical composition or dosage form is made to a body compartment, e.g., an intra-articular space, an epidural space or within the vitreous of the eye, there is an unexpected, long-term sustained release of the corticosteroid with minimal systemic impact.

The sustained release delivery mechanism is based on dissolution. While not wishing to be bound by any specific mechanism of action, it has been found that when crystalline corticosteroid drug particles coated with semi-permeable polymeric shells are injected into a body compartment, e.g., intra-articularly, water from the body compartment diffuses through the polymeric shell and partially dissolves the crystal drug core. As a result, a saturated solution of the drug is formed inside the polymeric shell. Since there are essentially sink conditions in the fluid (e.g., synovia when the body compartment is a joint) in which the microparticles are injected and reside, a concentration gradient is created which continuously drives the corticosteroid drug out of the microparticles and into the surrounding fluid. As long as there is some drug core remaining to maintain a saturated solution within the polymeric shell, a constant (i.e., zero order or pseudo-zero order) release of the drug from the coated microparticles is obtained.

Also disclosed herein is a method for reducing inflammation or managing pain, e.g. due to arthritis, by administering an injectable dosage form to a body compartment (e.g., intra-articular injection). Advantageously, the release is highly localized within the local tissue or fluid medium of the body compartment (e.g., synovium of synovial fluid) to ensure a long-acting local therapeutic level, while maintaining a low or undetectable systemic level of the corticosteroid.

Definitions

The articles "a" and "an" are used herein to refer to one or to more than one (i.e., to at least one) of the grammatical object of the article. By way of example, "an element" means one element or more than one element.

The term "plurality" means "two or more", unless expressly specified otherwise. For example, "plurality" may simply refer to a multiplicity of microparticles (two or more) or an entire population of microparticles in a given composition or dosage form, e.g., for purpose of calculating the size distribution of the microparticles.

As used herein, unless specifically indicated otherwise, the word "or" means "either/or," but is not limited to "either/or." Instead, "or" may also mean "and/or."

When used with respect to a therapeutic agent or a drug (e.g., a corticosteroids), the terms "sustained release" or "extended release" are used interchangeably. Sustained release refers to continuously releasing the therapeutic agent over an extended period of time after administration of a single dose, thus providing a prolonged therapeutic effect throughout the release period.

"Sustained release" is in contrast to a bolus type administration in which the entire amount of the active agent/substance is made biologically available at one time. Nevertheless, "sustained release" may include an initial faster release followed by a longer, extended period of slower release. As discussed in further detail below, the construction of the microparticles makes it possible to minimize the initial faster release (e.g., a burst release) and prolong the extended release period to achieve a profile of near constant release that is irrespective of the drug concentration (i.e., a zero-order or pseudo zero-order release).

Not all non-zero release is within the meaning of "sustained release." Rather, "sustained release" should provide at least a minimum therapeutically effective amount (as defined herein) of the corticosteroids during the release period. It should be understood that the minimum therapeutically effective amount of corticosteroid depends on the severity of the inflammation and/or pain to be addressed.

"Sustained release period" refers to the entire period of release during which a local concentration of the corticosteroid drug is maintained at or above a minimum therapeutically effective amount. The desired sustained-release period can, of course, vary with the disease or condition being treated, the nature of the corticosteroid, and the condition of the particular patient to be treated. Thus, the desired sustained-release period can be determined by the attending physician.

"Local concentration" refers to the concentration of the corticosteroid drug within a body compartment (as defined herein), including the concentration in the tissue or fluid of the body compartment.

"Plasma concentration" refers to the concentration of the corticosteroid drug in the plasma or serum. The injectable microparticles are capable of highly localized release during a prolonged period while maintaining a low plasma concentration, e.g., sufficiently low to minimize HPA axis suppression during the sustained release period. Plasma concentration below 75 pg/mL is considered below quantifiable limits (BQL), below 30 pg/mL is considered undetectable.

Within the scope of the present disclosure, sustained release of the corticosteroid is achieved due to the unique structure of the microparticles, which are in core/shell morphology. In particular, a crystalline drug core of a corticosteroid is encapsulated by a polymeric shell composed of one or more polymeric coatings, each permeable to the corticosteroid. In a preferred embodiment, all layers comprise the same polymer. In other embodiments, two to four layers of the polymer are coated on the corticosteroid, with each layer incrementally slowing the release of the active ingredient and collectively providing the desired sustained release. Furthermore, sustained release of the corticosteroid is achieved by tailoring this delivery platform to the aqueous or sink environment of the body compartment (e.g., synovium).

As used herein, a "patient," or "subject," to be treated by the methods according to various embodiments may mean either a human or a non-human animal, such as primates, mammals, and vertebrates.

The phrase "therapeutically effective amount" refers to an amount of a therapeutic agent that, when delivered to a body compartment (e.g., intra-articularly) in the form of the coated microparticles as defined herein, produces a degree of reduced inflammation or pain in the body compartment (e.g., a joint) in a patient (at a reasonable benefit/risk ratio applicable to any medical treatment). The effective amount of the therapeutic agent may vary depending on such factors as the type and severity of arthritis being treated, its advancement, the degree of pain to which patient is subject, the particular microparticle being administered, the active agent and/or the size/age/gender of the subject. One of ordinary skill in the art may empirically determine the effective amount of a particular therapeutic agent according to known methods in the art. Unless specified otherwise, "therapeutically effective amount" refers to the amount of the therapeutic agent localized within the body compartment.

"Minimum therapeutically effective amount" is the least amount of the therapeutic agent that is capable of producing a therapeutic effect (e.g., pain reduction or anti-inflammation).

"EC50" is the concentration of the therapeutic agent that provides 50% of the maximal effect, e.g., in reducing inflammation or pain.

"Unit dosage form" refers to physically discrete units (e.g., loaded syringe cylinders) suitable as unitary dosages for human subjects, each unit containing a predetermined quantity of the therapeutic agent in association with a pharmaceutical acceptable vehicle. The quantity of the therapeutic agent is calculated to produce the desired therapeutic effect for a desired period of time.

The term "treating" is art-recognized and includes treating the disease or condition by ameliorating at least one symptom of the particular disease or condition, even if the underlying pathophysiology is not affected.

"Body compartment" refers to a space or cavity within the body of a vertebrate (including human) that is accessible by injection. Typically, the body compartment is at least semi-enclosed or fully enclosed by hard or soft tissue (e.g., bones, membranes, ligamentous structure) that defines the space. Soft tissue is typically present and may have various degrees of vascularization. The body compartment typically contains a fluid, such as the synovial fluid in the joints, spinal fluid in the epidural and the vitreous humour in the vitreous body of the eye. The fluid may or may not communicate with the outside of the body compartment. More specifically, the body compartment may be naturally occurring anatomical space such as a synovial joint, an epidural space or a vitreous body of an eye. In addition, the body compartment may also be a surgically created space (e.g., a pocket for inserting an implanted device, soft tissue implant such as breast implant, and the like) or any space near the implant that can be accessed through injection.

The term "synovial joint" refers to a moveable articulation of two or more bones. The articulation is defined by a synovial cavity, which contains a volume of synovial fluid, is lined with a synovial membrane, and is surrounded by a fibrous capsule. The opposing bone surfaces are each covered with a layer of cartilage. The cartilage and synovial fluid reduce friction between the articulating bone surfaces and enable smooth movements. Synovial joints can be further distinguished by their shape, which controls the movements they allow. For example, hinge joints act like the hinge on a door, allowing flexion and extension in just one plane. An example is the elbow between the humerus and the ulna. Ball and socket joints, such as the hip, allow movement in several planes simultaneously. Condyloid (or ellipsoid) joints, such as the knee, permit motion in more than one plane in some positions but not others. For example, no rotation is possible in the extended knee, but some rotation is possible when the knee is flexed. Pivot joints, such as the elbow (between the radius and the ulna), allow one bone to rotate around another. Saddle joints, such as at the thumb (between the metacarpal and carpal) are so named because of their saddle shape, and allow movement in a variety of directions. Finally, gliding joints, such as in the carpals of the wrist, allow a wide variety of movement, but not much distance.

Synovial joints include, but are not limited to, shoulder (glenohumeral and acromioclavicular), elbow (ulno-humeral, radio-capitellar and proximal radioulnar), forearm (radioulnar, radiocarpal, ulnocarpal), wrist (distal radioulnar, radio-carpal, ulno-carpal, mid carpal), hand (carpometacarpal, metocarpophalangeal, interphalangeal), spine (intervertebral), hip, knee, ankle (tibiotalar, tibiofibular), and foot (talocalcaneal, talonavicular, intertarsal, tarso-metatarsal, metatarsal-phalangeal, interphalangeal).

"Intra-articular" and "intravitreous" are used herein interchangeably to mean within the vitreous humour of the eye.

As used herein, the term "microparticle" means a particle having mean dimension less than 1 mm. Although the microparticles are substantially spherical in some embodiments, the microparticles can be any solid geometric shape which is not inconsistent with the principles of the disclosure, including, without limitation, needles, ellipsoids, cylinders, polyhedrons and irregular shapes.

Microparticles are coated crystalline drug particles. As used herein, a microparticle has a "core/shell" morphology, shown schematically in FIG. 1, in which the drug core (10) is encapsulated by a polymeric shell (20), the polymeric shell may include one or more thin coatings of the same or different polymers (two coatings, 25 and 30, are shown). Importantly, the polymeric shell (20) is formed of polymer coatings that are not miscible with the drug core, thus, the interface (40) between the drug core and the polymeric shell is sharp with minimal amounts of drug or polymer (e.g., less than 5%, or less than 1% or less than 0.5% of the total weight of either the drug or polymer shall be mixed). Because the drug core contains a highly hydrophobic corticosteroid drug, the polymeric shell includes at least one hydrophilic polymer. Although the polymeric shell may be ultimately degraded, it should maintain its structural integrity throughout the sustained release period, thus retaining an environment for the dissolving drug core to form a saturated solution.

As used herein, the term "active pharmaceutical ingredient," "therapeutic agent," or drug, means one or more corticosteroids. As used herein, corticosteroid means fluticasone or a pharmaceutically acceptable salt or ester thereof. More specifically, the corticosteroid may be at least one of fluticasone, fluticasone furoate, and fluticasone propionate, derivatives, or pharmaceutically acceptable salts or esters thereof.

As used herein, the terms "crystalline drug core," "core particle," and "drug core" interchangeably refer to a pre-formed particle that includes a single crystal or multiple crystals of the drug. The drug core is encapsulated by a polymeric shell. The core particle can further comprise other compounds, including, without limitation, binders, buffers, antioxidants, excipients, and additional active pharmaceutical ingredients. The core particle can be a single large crystal, a multiplicity of crystals, or mixtures of the above. In a preferred embodiment, the drug core is substantially pure drug (i.e., at least 90%, or at least 95% or at least 98% of the entire weight of the drug core is the drug). In a preferred embodiment, the drug core is 100% crystalline drug.

As used herein, "polymeric shell" includes one or more polymeric coatings. "Polymeric coating" means a thin layer of linear, branched or cross-linked macromolecules that has a continuous surface surrounding the crystalline drug core. Referring to FIG. 1, the polymeric coatings (25 and 30) are sequentially and concentrically coated on the drug core (20). Although the drug core (20) and the immediate adjacent polymeric coating (25) should be immiscible, the polymeric coatings (25 and 30) themselves may be in intimate contact with each other, allowing for certain degrees of miscibility at the interface (50) between adjacent coatings in order to form a polymeric shell (20) of a cohesive structure that affords structural integrity during the sustained release period. The polymeric shell must substantially surround or envelope the core particles.

"Coating solution" refers to a solution of pre-formed polymers (e.g., commercially available polymers) and is suitable for coating the drug core according to known methods of the art, e.g. fluidized bed coating.

As used herein, the term "permeable" means allowing the passage of molecules of the therapeutic agent by diffusion but not by fluid flow.

As used herein, the term "semi-permeable" means permeable to some molecules but not to others. As used herein, semi-permeable polymeric shell are permeable to at least water and the therapeutic agent within the coated microparticles of the disclosure.

"Dissolution half-life" is an in vitro measurement of the dissolution characteristics of the microparticles. Specifically, the dissolution half-life is the amount of time that is taken for half of the original loading of the drug in the microparticles to dissolve and release into a dissolution medium under a specific set of dissolution conditions. Although carried out in vitro, the dissolution half-life is nevertheless an art-recognized factor to consider in predicting in vivo release characteristics and can represent an accelerated model of the sustained release behavior in vivo. In particular, dissolution half-life provides a qualitative tool for predicting in vivo behaviors by comparing the dissolutions half-lives of various formulations. For instance, formulations that exhibit a longer dissolution half-life in vitro are expected to exhibit a longer sustained release period in vivo. Unless specified otherwise, the dissolution system used for measuring dissolution half-life the microparticles is USP Type II (paddle).

"Dissolution profile" is a graphic representation of the percentage dissolution as measured by time. Besides providing quantitatively the dissolution amount as a function of time, the curvature of the profile qualitatively shows the extent of the initial burst. For example, a sharp rise in the curvature indicates a faster initial release (burst) when compared with a gentler rise.

"Vehicle" refers to a non-toxic carrier, adjuvant, or solvent into which the microparticles are suspended. The vehicle does not alter or destroy the pharmacological activity of the therapeutic agent with which it is formulated. Pharmaceutically acceptable carriers or vehicles that may be used in the compositions include, but are not limited to, water, physiological saline, hyaluronic acid, and the like. As used herein, the term "biocompatible" means characterized by not causing a toxic, injurious or immunological response when brought into contact with living tissue, particularly human or other mammalian tissue.

As used herein, the term "biodegradable" means capable of partially or completely dissolving or decomposing in living tissue, particularly human or other mammalian tissue. Biodegradable compounds can be degraded by any mechanism, including, without limitation, hydrolysis, catalysis and enzymatic action.

As used herein with respect to polymeric coatings, the term "substantially degraded" means degraded to the degree that approximately 50% of the chemical bonds resulting from polymerization of the polymer-forming solution to form the polymeric coating have been broken.

As used herein with respect to the polymeric shell of the disclosure, the term "structural integrity" means retaining a continuous surface which is semi-permeable and permits diffusion, but does not include any discontinuities which permit fluid flow.

As used herein, the term "external environment" means the local area or region of tissue surrounding the coated microparticles of the disclosure after direct injection into the body compartment.

As used herein, the term "saturated" means containing the maximum concentration of a solute (e.g., an active pharmaceutical ingredient) that can be dissolved at a given temperature.

As used herein, the term "substantially insoluble" means having a solubility of less than 1 part solute per 1000 parts solvent by weight.

As used herein, the term "hydrophobic" means having lower affinity for an aqueous solvent than an organic solvent.

As used herein, the term "hydrophilic" means having lower affinity for an organic solvent than an aqueous solvent.

As used herein, term "pseudo-zero-order kinetics" means sustained-release of the active pharmaceutical ingredient (corticosteroid) which exhibits kinetics which is zero-order (i.e., independent of concentration) or between zero-order and first-order (i.e., proportional to concentration) kinetics over the sustained-release period, where the concentration is based on the total amount of the active pharmaceutical ingredient contained within the coated microparticles. In some embodiments, the release of the active pharmaceutical ingredient exhibits kinetics which more closely approximate zero-order than first-order kinetics.

As used herein, the recitation of a numerical range for a variable is intended to convey that the disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values and if the variable is inherently continuous.

Microparticles

The microparticles of the core/shell morphology described herein are constructed to exhibit a sustained release profile uniquely suited for highly localized, extended delivery of a corticosteroid drug within a body compartment. In particular, the microparticle includes (1) a crystalline drug core of more than 70% by weight of the microparticle, wherein the crystalline drug core includes one or more crystals of fluticasone or a pharmaceutically acceptable salt or ester thereof; and (2) a polymeric shell encapsulating the crystalline drug core, whereby the polymeric shell is in contact but immiscible with the crystalline drug core.

The in vivo sustained release profile is correlatable to the in vitro dissolution characteristics of the microparticles, which in turn are determined by, among others, the solubility of the drug core, the permeability, the level of crosslinking and the rate of degradation of the polymeric shell. Due to a precision heat-treatment step in the formation, the microparticles described herein unexpectedly have a long dissolution half-life of 12-20 hours, when tested using United States Pharmacopoeia Type II apparatus wherein the dissolution conditions are 3 milligrams of microparticles in 200 milliliters of dissolution medium of 70% v/v methanol and 30% v/v of water at 25° C. These features are discussed in more detail below.

Crystalline Drug Core

The crystalline drug core according to the embodiments of this disclosure is a corticosteroid drug. More specifically, the crystalline drug core comprises at least one of fluticasone, or a pharmaceutically acceptable salt or ester thereof. More specifically, the core comprises at least one of fluticasone, fluticasone furoate, and fluticasone propionate. Most preferably, the corticosteroid is fluticasone propionate.

As the preferred system is for formulating corticosteroids, and as this is a "dissolution based delivery system," corticosteroids of relative low solubility are preferred. Fluticasone in general and fluticasone propionate in particular are ideal in this regard due to potency and high degree of insolubility. Johnson M. Development of fluticasone propionate and comparison with other inhaled corticosteroids. *The Journal of allergy and clinical immunology* 101(4 Pt 2):5434-9, 1998.

The crystalline form of the corticosteroid drug has even lower solubility than the amorphous form of the same drug, resulting in a longer dissolution half-life and less initial burst. Accordingly, the drug core may be a single large crystal or an aggregation of multiple small crystals. Crystalline drug core coated with a polymeric shell further extends the period of dissolution and further minimizes any initial burst.

The exact anti-inflammatory mechanism of action of corticosteroids is unknown. However, it is well known that steroids have many potentially anti-inflammatory actions, and they inhibit the expression and action of many proinflammatory cytokines. Brattsand R, et al. Cytokine modulation by glucocorticoids: mechanisms and actions in cellular studies. *Alimentary Pharmacology & Therapeutics* 2:81-

90, 1996. Glucocorticoids modulate cytokine expression by a complex combination of genomic mechanisms, and the activated glucocorticoid receptor complex can bind to and inactivate key pro inflammatory transcript factors. In addition, inflammation can be suppressed via glucocorticoid responsive elements (GRE) which up-regulate the expression of cytokine inhibitory proteins. In studies with triggered human blood mononuclear cells in culture, glucocorticoids strongly diminished production of the initial phase cytokines IL-1 beta and TNF alpha, immunomodulatory cytokines IL-2, IL-3, IL-4, IL-6 IL-10, IL-12 and INF gamma, as well as IL-6, IL-8 and the growth factor GM-CSF. Cato AC et al. Molecular mechanisms of anti-inflammatory action of glucocorticoids. *Biochemical Society Transactions* 18(5):371-378, 1996. In addition to diminishing the production of cytokine, steroids can also inhibit its subsequent actions. Because cytokines work in cascades, this means that steroid treatment can block expression of the subsequent cytokines. This blocked cytokine activity does not depend on a reduced cytokine receptor expression, but may be associated with receptor up regulation. Jusko W J. Pharmacokinetics and receptor-mediated pharmacodynamics of corticosteroids. *Toxicology* 102(1-2):189-196, 1995.

The therapeutic agents are used in amounts that are therapeutically effective, which varies widely depending largely on the particular agent being used. The amount of agent incorporated into the composition also depends upon the desired release profile, the concentration of the agent required for a biological effect, and the length of time that the biologically active substance has to be released for treatment.

There is no critical upper limit on the amount of therapeutic agent incorporated except for that of an acceptable solution or dispersion viscosity to maintain the physical characteristics desired for the composition. The lower limit of the agent incorporated into the polymer system is dependent upon the activity of the corticosteroid and the length of time needed for treatment. Thus, the amount of the corticosteroid should not be so small that it fails to produce the desired physiological effect, nor so large that it is released in an uncontrollable manner.

A key advantage of the injectable microparticles lies in the much higher drug loading than previously known drug-loaded microparticles. In other words, each microparticle has a comparatively and significantly smaller fraction as the polymeric shell, and a comparatively and significantly greater fraction as the corticosteroid core.

Moreover, the drug core is substantially pure drug as the drug core is prepared from recrystallized drug in the form of either a single large crystal or an aggregate of smaller crystals. Thus, "substantially pure" means at least 90%, or at least 95% or at least 98%, or 100% of the entire weight of the drug core is the drug in a crystalline form.

Thus, in various embodiments, in each microparticle, 70-97% of the total weight of microparticle is corticosteroid and 3-30% is polymer. In one embodiment, the drug core is more than 70% of the total weight of the microparticle and less than 30% of the total weight of the microparticle is the polymeric shell. In other embodiments, the drug core is more than 75%, more than 80%, more than 85%, more than 90% or more than 95% of the total weight of the microparticle, with the remainder of the microparticle being the polymeric shell.

Polymeric Shell

The polymeric shell comprises one or more concentrically or consecutively coated polymeric coatings of the same or different polymers. Standard biocompatible and biodegradable polymeric coatings known in the art can be employed to the extent that they meet the requirements described above with respect to retaining permeability and/or structural integrity during the desired sustained-release period. While the sustained release period is enhanced within the scope of the disclosure via higher drug loading and the beneficial and unexpected interaction of the body compartment (e.g., synovial environment) and the dissolution-based delivery system described herein, there are additional factors at play supporting the superior efficacy of the method herein including, but not limited to:

the degree of solubility of the corticosteroid the rate of clearance of the corticosteroid from the synovium the size of the core particle and/or the amount of the corticosteroid initially present in the core particle the presence of other compounds within the core particle that affect the rate of release of the corticosteroid the permeability of the polymeric coating(s) to the corticosteroid the rate of degradation of the polymeric coating(s), as well as other factors.

As is known in the art, both the permeability and biodegradability of polymeric coatings can be affected by the choice of polymeric material (e.g., degree of hydrophobicity or hydrophilicity relative to the corticosteroid; degree of lability of bonds under physiological conditions), degree of cross-linking and thickness. For co-polymers, the ratio of the different monomers also can be varied to affect permeability and biodegradability.

In preferred embodiments, suitable biocompatible and biodegradable polymers include polyvinyl alcohol (PVA), poly(p-xylylene) polymers (trademarked as Parylene®), poly(lactic acid) (PLA), poly(glycolic acid) (PGA), poly (lactic-co-glycolic acid) (PLGA), poly(ε-caprolactone) (PCL), poly(valerolactone) (PVL), poly(ε-decalactone) (PDL), poly(1,4-dioxane-2,3-dione), poly(1,3-dioxane-2-one), poly(para-dioxanone) (PDS), poly(hydroxybutyric acid) (PHB), poly(hydroxyvaleric acid) (PHV), ethylene vinyl acetate (EVA) and poly(β-malic acid) (PMLA).

In order to affect permeability and release rates, the polymeric coatings can optionally be covalently or ionically cross-linked. For example, monomers can be chosen which include chemical groups which are capable of forming additional bonds between monomers, or separate cross-linking agents can be included in the polymer-forming solutions in addition to the monomers. In some embodiments, the cross-linking groups are thermally activated, whereas in other embodiments they are photoactivated, including photoactivation by visible or ultraviolet radiation. Cross-linking groups include, without limitation, unsaturated groups such as vinyl, allyl, cinnamate, acrylate, diacrylate, oligoacrylate, methacrylate, dimethacrylate, and oligomethoacrylate groups. As many corticosteroids are hydrophobic, and because it is desirable to reduce or avoid dissolution of the drug core into the polymeric shell in order to maintain a sharp interface between the core and shell, the polymeric shell should include a hydrophilic polymer, particularly in the coating that is most proximate to the crystalline core. Examples of hydrophilic polymeric coatings include, without limitation, poly(vinyl alcohol) (PVA), poly (ethylene glycol) (PEG), poly(ethylene oxide), poly(vinylpyrrolidone), poly(ethyloxazoline), or polysaccharides or carbohydrates such as alkylcelluloses, hydroxyalkylcelluloses, hyaluronic acid, dextran, heparan sulfate, chondroitin sulfate, heparin, or alginate, or proteins such as gelatin, collagen, albumin, ovalbumin, or polyamino acids.

Additional examples of suitable polymers can be prepared from monomers selected from the following group: sugar phosphates, alkylcellulose, hydroxyalkylcelluloses, lactic acid, glycolic acid, β-propiolactone, β-butyrolactone, γ-butyrolactone, pivalolactone, α-hydroxy butyric acid, α-hydroxyethyl butyric acid, α-hydroxy isovaleric acid, α-hydroxy-β-methyl valeric acid, α-hydroxy caproic acid, α-hydroxy isocaproic acid, α-hydroxy heptanic acid, α-hydroxy octanic acid, α-hydroxy decanoic acid, α-hydroxy myristic acid, α-hydroxy stearic acid, α-hydroxy lignoceric acid and β-phenol lactic acid.

Because the crystalline drug core is comprised of at least 70% by weight of the microparticles, the overall sizes of the microparticles are largely determined by the size of the crystalline drug core. Typically, the polymeric shell has a thickness of about less than 12%, or less than 5% or less than 3% of the total diameter of the microparticle. Likewise, the weight of the microparticle is also predominately the weight of the crystalline core, resulting in a high drug loading. In preferred embodiments, the microparticle comprises 90-98% w/w of crystalline drug core and 2-10% w/w of polymeric shell.

In various embodiments, the microparticles have a mean diameter of between 50 μm and 800 μm, or a mean diameter of between 60 μm and 250 μm, or a mean diameter of between 80 μm and 150 μm.

In a preferred embodiment, the mean diameter is 150 μm with a standard deviation of less than 50% of the mean diameter. In another preferred embodiment, the mean diameter is 75 μm with a standard deviation of less than 50% of the mean diameter.

Methods of Forming Microparticles

Methods of forming polymeric coatings on particles are well known in the art. For example, standard techniques include solvent evaporation/extraction techniques, in-water drying techniques (see, e.g., U.S. Pat. No. 4,994,281), organic phase separation techniques (see, e.g., U.S. Pat. No. 5,639,480), spray-drying techniques (see, e.g., U.S. Pat. No. 5,651,990), air suspension techniques, and dip coating techniques.

In a most preferred form, the method of forming microparticles as described in U.S. Patent Publication 2007/003619, which is fully incorporated herein by reference. The crystalline drug core is coated with one or more layers of polymeric coatings, which together form the polymeric shell. For example, in one aspect, a PVA polymeric coating can be applied using a dip coating technique. In brief, a 1% coating solution of PVA in water can be formed by dissolving excess PVA in water at 60° C. for 2 h (see, e.g., Byron and Dalby (1987), J. Pharm. Sci. 76(1):65-67). Alternatively, a higher concentration PVA solution (e.g., 3-4%) can be prepared in a reflux with heating to approximately 90-100° C. After cooling, the microparticles can be added to the PVA solution and agitated by, for example, swirling or stirring. The microparticles are then removed from the solution by, for example, filtration on filter paper with a mesh size appropriate to the microparticles. Optionally, vacuum-filtration can be employed to assist in drying. Untreated, PVA polymeric coatings or films are readily permeable to water and hydrophilic drugs. Heating of PVA, however, causes an increase in crystallinity and decrease of permeability of up to 500-fold with increasing temperatures in the range of 100-250° C. for periods of 0-160 hours (Byron and Dalby (1987), supra). Thus, in some embodiments, PVA polymeric coatings can be heated to temperatures between 100° C. and 250° C., between 125° C. and 175° C., or between 155° C. and 170° C. for periods between 1 sec. and 160 hours, between 1 min. and 10 hours, or between 5 minutes and 2 hours. Most preferably, heating is to 220° C. for one hour. Optionally, the coating process can be repeated several times to build-up a thicker polymeric coating. Most preferably, 2-5 coatings are applied to achieve a 5% thickness of coating.

In one embodiment, the microparticles undergo a precision heat treatment step at a temperature within the range of 210-230° C. for at least one hour. It is unexpectedly discovered that the level of crosslinking, and hence permeability, can be precision controlled by heating the microparticles within this temperature range. More preferably, the heat treatment step is carried out at 220° C. for one hour. As discussed in further detail below in connection with the dissolution characteristics and Example 6, heat-treated microparticles at a particular temperature range (210-230° C.) surprisingly attain a level of crosslinking and permeability that are capable of significantly enhancing the dissolution half-life.

In Vitro Dissolution Characteristics

The structure of the microparticles makes it possible for a highly localized delivery system based on dissolution. Accordingly, in vitro dissolution characteristics, such as dissolution half-life are correlatable to the sustained release period in vivo.

It is important to recognize that dissolutions models are designed to give an accelerated dissolution as compared to in vivo release. An IVIVC that mirrored the actual in vivo dissolution could take months to complete. Nevertheless, an accelerated USP type II standard dissolution is useful to provide a qualitative comparison among various formulations and to offer a predicator for the in vivo release behaviors.

Figure 2:
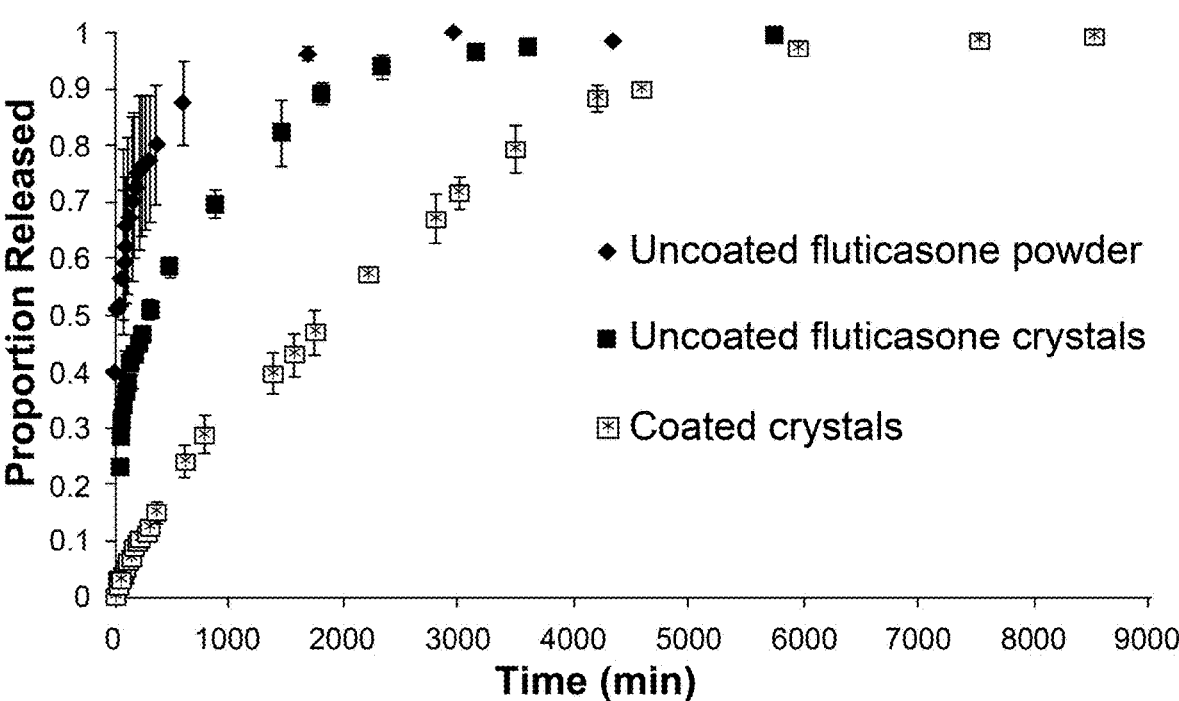
FIG. 2 shows the in vitro release profiles of fluticasone propionate as uncoated powder, uncoated crystal and coated crystal.

FIG. 2 shows the effect of the microparticle structures on dissolution rates. More specifically, FIG. 2 shows the in vitro release profiles of uncoated fluticasone propionate powder (amorphous or very small crystals), uncoated fluticasone propionate crystals and coated fluticasone propionate crystals. The dissolution profiles clearly show a trend of longer dissolution half-life and less initial burst in the crystalline drug as compared to amorphous drug. The trend is more pronounced for the coated crystalline drug compared to the uncoated crystalline drug. Additional details of the dissolution conditions are described in the Example sections.

Figures 3A, 3B:
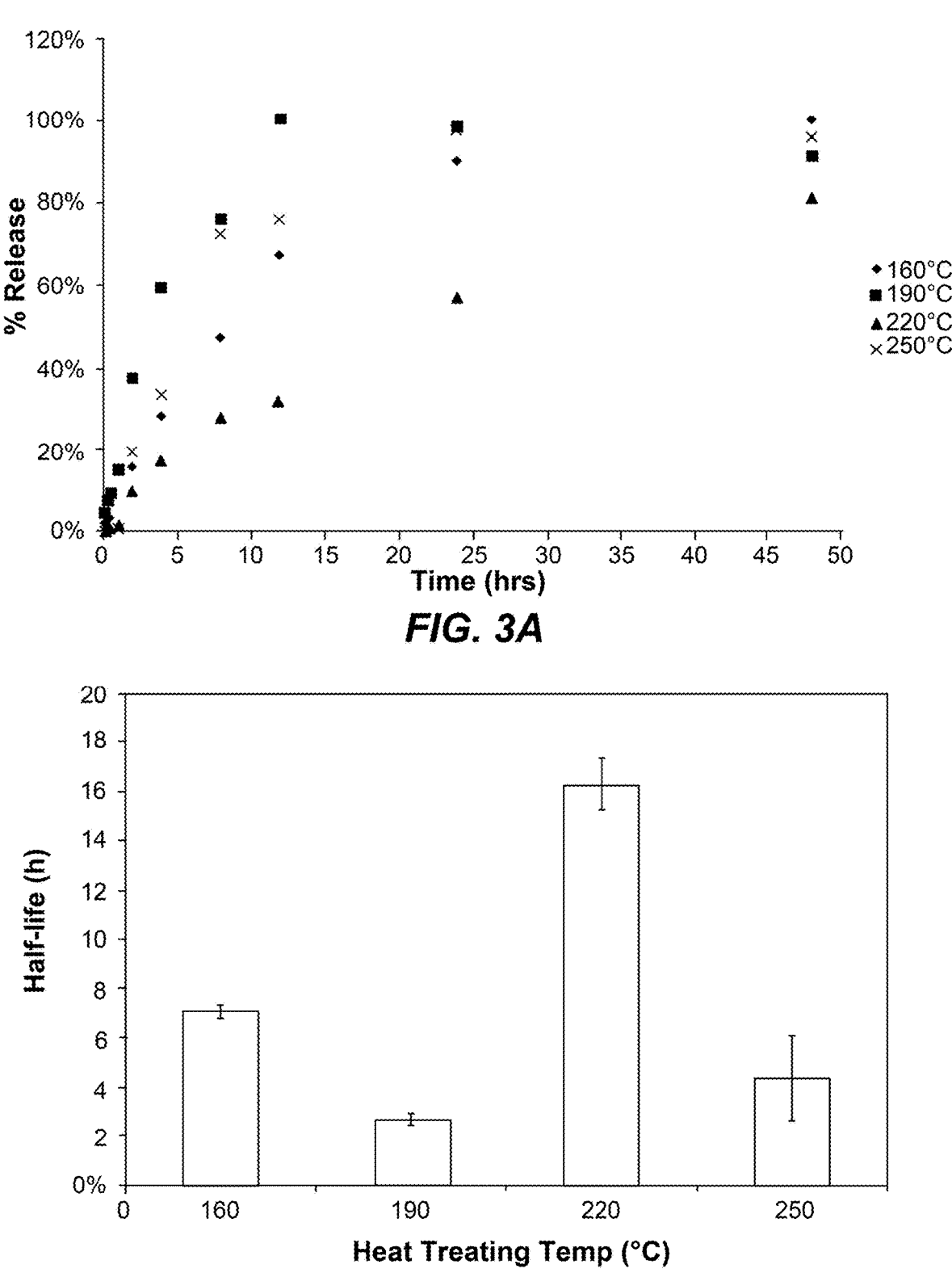
FIG. 3A shows the release profiles of fluticasone propionate microparticles having undergone heat-treatment at various temperatures.
FIG. 3B shows the release half-lives of fluticasone propionate microparticles having undergone heat-treatment at various temperatures.

The process of forming the microparticles also has a profound impact on the dissolution characteristics. In particular, a precision heat-treatment within a narrow temperature range (e.g., 210-230° C.) unexpectedly provides a significantly enhanced dissolution half-life when compared to those of microparticles having undergone heat treatment at temperatures outside of this range. In a dissolution test using United States Pharmacopoeia Type II apparatus, wherein the dissolution conditions are 3 milligrams of microparticles in 200 milliliters of dissolution medium of 70% methanol and 30% of water at 25° C., the dissolution profiles of microparticles that have undergone heat treatments at 160° C., 190° C., 220° C. and 250° C. are shown in FIG. 3A. Microparticles heat-treated at 220° C. have the slowest and gentlest initial release, as compared to those of microparticles treated at temperature above or below 220° C. FIG. 3B shows the dissolution half-lives of the microparticles of FIG. 3A. As shown, microparticles heat-treated at 220° C. have a significantly longer dissolution half-life (12-20 hours) than those of the other microparticles (all less than 8 hours).

The result indicates that precision thermal processing (i.e., heating within a narrow range of temperature for a specific period of time) afford certain structural characteristics (including, e.g., degrees of crosslinking, crystallinity, porosity and/or permeability) that are most effective in enhancing the dissolution half-life, and by extension, the sustained release period.

In Vivo Release Characteristics

Preliminary animal studies indicate that corticosteroid microparticles described herein are capable of highly localized sustained releasing of the corticosteroid drug within a body compartment (e.g., an intra-articular space) for 2-12 months after a single injection, or more typically, for 2-9 months, or for 3-6 months after a single injection. The results are discussed in more detail in Examples 10-13.

Even as the local concentrations exceed the EC50 of corticosteroid, the plasma concentration of the corticosteroid drug unexpectedly remains much lower than the local concentrations at any given time during the sustained release period and can be below quantifiable limit after 7 days. The low plasma concentration minimizes any clinically significant HPA axis suppression.

Moreover, the corticosteroid microparticles do not exhibit any significant initial burst (locally or systemically), unlike known drug-loaded microparticles.

The in vivo release characteristics confirm the release mechanism of pseudo-zero order, by which the corticosteroid drug is released at a nearly constant rate so long as a saturated solution can be maintained within the polymeric shell (e.g., for more than 60 days or for more than 90 days, or for more than 180 days), irrespective of the original drug loading. See also Examples 10-13.

Further, the in vivo release behaviors are correlatable to the in vitro dissolution behaviors. In particular, microparticles that have undergone heat-treatments at different temperatures (220° C. vs. 130° C.) exhibited in vivo release behaviors that are consistent with their in vitro dissolutions. See also, Examples 8 and 11.

Pharmaceutical Composition

One embodiment provides a pharmaceutical composition comprising: a plurality of microparticles, the microparticle including 1) a crystalline drug core of more than 70% by weight of the microparticle, wherein the crystalline drug core includes one or more crystals of fluticasone or a pharmaceutically acceptable salt or ester thereof; and (2) a polymeric shell encapsulating the crystalline drug core, wherein the polymeric shell is in contact but immiscible with the crystalline drug core, wherein said composition when dissolution tested using United States Pharmacopoeia Type II apparatus exhibits a dissolution half-life of 12-20 hours, wherein the dissolution conditions are 3 milligrams of microparticles in 200 milliliters of dissolution medium of 70% methanol and 30% of water at 25° C.

In a preferred embodiment, the crystalline drug core comprises at least one of fluticasone, fluticasone furoate, and fluticasone propionate.

In certain embodiments, the microparticles have undergone a heat-treatment step within a temperature range of 210-230° C.

In various embodiments, the mean diameters of the microparticles are in the range between 50 μm and 800 μm, or in the range between 60 μm and 250 μm, or in the range between 80 μm and 150 μm.

In further embodiments, the crystalline drug core is more than 75%, more than 80%, more than 85%, more than 90% or more than 95% of the total weight of the microparticle, with the remainder of the microparticles being the polymeric shell.

In various embodiments, at least 90%, at least 95%, at least 98%, or 100% of the entire weight of the drug core is the drug in a crystalline form.

In preferred embodiments, the diameters of the microparticles in a given pharmaceutical composition may be tailored or selected to suit a particular route of administration. Thus, one embodiment provides an injectable composition, in which more than 90% of the microparticles have diameters in the range of 100-300 µm, which are particularly suitable for an epidural injection. Another embodiment provides an injectable composition comprising microparticles in which more than 90% of the microparticles have diameters in the range of 50-100 µm, which are particularly suitable for intra-articular or intra-ocular injection.

Because the dissolution rate of the crystalline drug is related to the size of the crystals, i.e., the smaller the crystals, the higher the initial burst rate (see FIG. 2), it is preferred that the population of microparticles in a pharmaceutical composition has a narrow size distribution. Thus, in one embodiment, the plurality of microparticles in the pharmaceutical composition have a mean diameter in the range of 50 µm to 300 µm and a standard deviation of less than 50% of the mean diameter.

In a preferred embodiment, the mean diameter is 150 µm with a standard deviation of less than 50% of the mean diameter (e.g., for epidural injections). In another preferred embodiment, the mean diameter is 75 µm with a standard deviation of less than 50% of the mean diameter (e.g., for intra-articular or intra-ocular injections).

In a further embodiment, the pharmaceutical composition further comprises a pharmaceutically acceptable vehicle, in which the plurality of microparticles is suspended. It is preferred that the microparticles of corticosteroid are mixed with the vehicle immediately prior to injection, so there is no time for the corticosteroid to dissolve into the vehicle and there is no or substantially no initial burst of drug prior to injection.

Unit Dosage Form

A unit dosage form is a pharmaceutical composition (including all the embodiments as described above) having a predetermined quantity of corticosteroid microparticles which, after a single injection, provides sustain release of the corticosteroid for a specified period. The quantity of the corticosteroid microparticles in a unit dosage will depend upon several factors including the routes of administration (intra-articular, intra-epidural, or intra-ocular), the body weight and the age of the patient, the severity of inflammation or pain, or the risk of potential side effects considering the general health status of the person to be treated.

Advantageously, because the corticosteroid microparticles described herein are capable of near zero-order release with little initial burst, the initial loading the drug in the unit dosage form can be rationally designed according to the desired sustained release period.

Thus, one embodiment provides an injectable unit dosage form of a corticosteroid for injecting into a body compartment, the injectable unit dosage form comprising: a plurality of microparticles, the microparticle including (1) a crystalline drug core of more than 70% by weight of the microparticle; and (2) a polymeric shell encapsulating the crystalline drug core, wherein the crystalline drug core includes one or more crystals of a corticosteroid selected from fluticasone, fluticasone furoate, and fluticasone propionate, and the polymeric shell is in contact but immiscible with the crystalline drug core, wherein the injectable dosage form is capable of sustained-release of the corticosteroid for a period of 2-20 months while maintaining a minimum therapeutically effective concentration of the corticosteroid within the body compartment.

In a further embodiment, the sustained release period is 2-9 months.

In a further embodiment, the sustained release period is 3-6 months.

In other embodiment, the plasma concentration of the corticosteroid is below quantifiable level after 7 days.

In various embodiments, the unit dosage form comprises 0.5-20 mg of corticosteroid. In other embodiments, the unit dosage form comprises 3-20 mg of corticosteroid.

In various embodiments, the unit dosage form further comprises a pharmaceutically acceptable vehicle. Preferably, the vehicle is combined with the corticosteroid microparticles immediately before injection to avoid dissolution of the drug into the vehicle. Advantageously, because of the lack of initial burst, any dissolution of the corticosteroid into the vehicle during normal handling time in preparation for an injection is insignificant. In contrast, many known drug-loaded sustained release formulations are capable of saturating the vehicle during handling time due to an initial burst.

Methods of Using and Routes of Administration

The pharmaceutical compositions and dosage forms described herein are designed to be injected into a body compartment for highly localized, sustained release of corticosteroid. The body compartment typically contains soft tissue and/or fluid within an enclosure or semi-enclosure. The injection is directed to the soft tissue or the fluid, into which the corticosteroid microparticles are released. When needed, the injection can be guided by an imaging system such as an ultrasonic or X-ray device.

In one embodiment, the injection is administered intra-articularly for sustained-release of a corticosteroid in the synovium or synovial fluid.

In another embodiment, the injection is administered into an epidural space for sustained-release of a corticosteroid.

In a further embodiment, the injection is administered intra-ocularly, or intra-vitreously for sustained-release of a corticosteroid in the vitreous humour.

In a further embodiment, the injection is administered to a surgically created pocket or a natural space near an implant for sustained-release of a corticosteroid therein for reducing pain and/or inflammation associated with capsule constriction (e.g., following implant) or keloid scar formation.

Diseases that May be Treated Using the Formulations of this Disclosure

Various embodiments provide long-acting treatments or therapies for reducing inflammation and/or pain. Although these embodiments are exemplified with reference to treat joint pain associated with osteoarthritis, rheumatoid arthritis and other joint disorders, it should not be inferred that the disclosure is only for these uses. Rather, it is contemplated that embodiments of the present disclosure will be useful for treating other forms of pain and/or inflammation by administration into articular and peri-articular spaces, epidural space, vitreous humour of the eye, or space near an implant having scar tissue formation.

Thus, the diseases and conditions that may be treated by intra-articular injection of the pharmaceutical composition and unit dosage form described herein include, without limitation, osteoarthritis, rheumatoid arthritis or injury induced arthritis, Lupus, traumatic arthritis, polymyalgia rheumatica, post-operative joint pain, facet joint disease/inflammation, tensynovitis, bursitis, fasciitis, ankylosing spondylitis.

In other embodiments, the diseases and conditions that may be treated by an injection to the epidural space include, without limitation, spinal disc protrusion, spinal nerve inflammation in cervical, thoracic or lumbar, chronic low back pain from nerve root compression.

In other embodiments, the diseases and conditions that may be treated by an intra-ocular or intra-vitreous injection include, without limitation, diabetic macular edema and uveitis.

In other embodiments, the diseases and conditions that may be treated by an injection into a space near an implant having scar tissue formation for releasing pain and inflammation are related to recurrent capsular contractions (e.g., breast implant) and for keloid scarring control.

Thus, one embodiment provides a method of treating inflammation or managing pain in a body compartment of a patient in need thereof, comprising injecting to the body compartment a therapeutically effective amount of pharmaceutical composition having a plurality of microparticles, the microparticle including 1) a crystalline drug core of more than 70% by weight of the microparticle, wherein the crystalline drug core includes one or more crystals of fluticasone or a pharmaceutically acceptable salt or ester thereof; and (2) a polymeric shell encapsulating the crystalline drug core, wherein the polymeric shell is in contact but immiscible with the crystalline drug core.

In a preferred embodiment, the crystalline drug core comprises at least one of fluticasone, fluticasone furoate, and fluticasone propionate.

In various embodiments, the microparticles have undergone a heat-treatment step within a temperature range of 210-230° C.

In various embodiments, the mean diameters of the microparticles are in the range between 50 μm and 800 μm, or in the range between 60 μm and 250 μm, or in the range between 80 μm and 150 μm.

In preferred embodiments, the diameters of the microparticles in a given pharmaceutical composition may be tailored or selected to suit a particular route of administration. Thus, one embodiment provides an injectable composition, in which more than 90% of the microparticles have diameters in the range of 100-300 μm, which are particularly suitable for an epidural injection. Another embodiment provides an injectable composition comprising microparticles in which more than 90% of the microparticles have diameters in the range of 50-100 μm, which are particularly suitable for intra-articular or intra-ocular injection.

In further embodiments, the crystalline drug core is comprised of more than 75%, more than 80%, more than 85%, more than 90% or more than 95% of the total weight of the microparticle, while the remainder being the polymeric shell.

In various embodiments, at least 90%, at least 95%, at least 98%, or 100% of the entire weight of the drug core is the drug in a crystalline form.

In certain embodiments, said composition when dissolution tested using United States Pharmacopoeia Type II apparatus exhibits a dissolution half-life of 12-20 hours, wherein the dissolution conditions are 3 milligrams of microparticles in 200 milliliters of dissolution medium of 70% methanol and 30% of water at 25° C.

In other embodiments, said composition when dissolution tested using United States Pharmacopoeia Type II apparatus exhibits a dissolution half-life of 12-20 hours, wherein the dissolution conditions are 3 milligrams of microparticles in 200 milliliters of dissolution medium of 70% methanol and 30% of water at 25° C.

A specific embodiment further provides a method of decreasing inflammation and pain in a patient comprising administering to the patient in need thereof, via intra-articular injection, a therapeutically effective amount of a pharmaceutical preparation for sustained release of a corticosteroid comprising a multiplicity of coated microparticles, said coated microparticles having a mean diameter of 50 μm and 350 μm and wherein the microparticles are particles comprised of greater than 70% corticosteroid by weight.

Another embodiment provides a method of treating inflammation or managing pain in a body compartment of a patient in need thereof, comprising injecting to the body compartment a single injection of a unit dosage form having a plurality of microparticles, the microparticle including (1) a crystalline drug core of more than 70% by weight of the microparticle; and (2) a polymeric shell encapsulating the crystalline drug core, wherein the crystalline drug core includes one or more crystals of a corticosteroid selected from fluticasone, fluticasone furoate, and fluticasone propionate, and the polymeric shell is in contact but immiscible with the crystalline drug core, wherein the injectable dosage form is capable of sustained-release of the corticosteroid for a period of 2-12 months while maintaining a minimum therapeutically effective concentration of the corticosteroid within the body compartment.

Additional specific embodiments include:

said microparticles have a mean diameter of between 50 μm and 800 μm.

said microparticles have a mean diameter of between 60 μm and 250 μm.

said microparticles have a mean diameter of between 80 μm and 150 μm.

the corticosteroid is selected from the group consisting of fluticasone, fluticasone furoate, and fluticasone propionate.

the corticosteroid is a pharmaceutically acceptable ester prodrug of fluticasone (fluticasone propionate).

said preparation is administered at a site permitting direct interaction between said corticosteroid and an affected joint of said patient.

sustained release refers to at least three months.

wherein inflammation and pain is arthritic joint pain.

wherein said pharmaceutical preparation for sustained release comprises large particles of substantially pure corticosteroid coated with at least one biocompatible or bio-erodible polymer.

which reduces or eliminates an initial corticosteroid drug burst.

the polymer comprises at least one of polylactic acid, polyvinyl alcohol and Parylene™ the systemic levels of fluticasone administered in the method as described herein produce no clinically significant HPA axis suppression.

inflammation and pain in a patient is due to at least one of osteoarthritis, rheumatoid arthritis or injury induced arthritis.

there is at or near consistent and sustained release of a corticosteroid.

the disease progression is slowed or halted due to the maintaining of the constant low level of steroid in the joint space the particles of corticosteroid are mixed with the vehicle immediately prior to injection, so there is no time for the corticosteroid to dissolve into the vehicle and there is no or substantially no initial burst of drug.

the present method has fewer systemic side effects than other therapies

Within the scope of the present disclosure, the corticosteroid is selected from the group consisting of fluticasone, fluticasone furoate, and fluticasone propionate. More preferably:

the corticosteroid is fluticasone propionate.

diffusion of said corticosteroid across said first polymeric coating exhibits pseudo-zero-order kinetics during said sustained-release period.

said first polymeric coating is not degraded until AFTER a sustained release period (which is a point of differentiation as compared to other sustained release formulations)

said first polymeric coating maintains structural integrity during said sustained-release period.

said microparticles have a maximum dimension between 50 μm and 250 μm.

said microparticles have a maximum dimension between 50 μm and 150 μm.

said corticosteroid is substantially insoluble in said coating solution.

said corticosteroid is hydrophobic and said first coating solution is hydrophilic.

The polymeric shell comprises one or more polymeric coatings that are the same or different and may comprise a polymer or co-polymer including at least one monomer selected from the group consisting of sugar phosphates, alkylcellulose, hydroxyalkylcelluloses, lactic acid, glycolic acid, β-propiolactone, β-butyrolactone, γ-butyrolactone, pivalolactone, α-hydroxy butyric acid, α-hydroxyethyl butyric acid, α-hydroxy isovaleric acid, α-hydroxy-β-methyl valeric acid, α-hydroxy caproic acid, α-hydroxy isocaproic acid, α-hydroxy heptanic acid, α-hydroxy octanic acid, α-hydroxy decanoic acid, α-hydroxy myristic acid, α-hydroxy stearic acid, α-hydroxy lignoceric acid, β-phenol lactic acid, ethylene vinyl acetate, and vinyl alcohol.

the polymeric coating is applied to said core particles by an air suspension technique.

said polymeric coating is applied to said core particles by a dip coating technique.

These and other changes can be made to the present systems, methods and articles in light of the above description. In general, in the following claims, the terms used should not be construed to limit the disclosure to the specific embodiments disclosed in the specification and the claims, but should be construed to include all possible embodiments along with the full scope of equivalents to which such claims are entitled. Accordingly, the disclosure is not limited by the disclosure, but instead its scope is to be determined entirely by the following claims.

EXAMPLES

Example 1

General Procedure for Preparing Crystalline Drug Core

To fluticasone propionate (FP) powder (1 g), methanol (100 mL) is added and the suspension heated with stirring until a clear solution is obtained. The flask is left at room temperature over-night resulting in the formation of needle-shaped crystals. The crystals are collected using a Buchner funnel and thoroughly oven-dried at 40-50° C. for 2 h. The dry FP particles are added to an 80-170 μm mesh sieve along with a monolayer of glass beads. A 30-60 μm mesh sieve is added below the sieve containing the FP particles and beads, followed by shaking for 3-4 min. The 80-170 μm mesh sieve is replaced with a clean 80-170 μm mesh sieve, a 2000 μm mesh sieve added to the top (optional), and the sieve stack attached to a Buchner funnel. The content of the 80-170 μm mesh sieve containing the FP particles and beads is gently poured into the 2000 μm mesh sieve to collect the glass beads and washed with deionized water (DI-$H_2O$) under suction. The 2000 μm mesh sieve is removed and the content of the 80-150 μm mesh sieve washed with DI-$H_2O$ under suction. A total of 200-300 mL of DI-$H_2O$ typically is used. Alternatively, the content of the sieves may be washed with TWEEN-80 (0.1% w/v) before washing with water, or the glass beads are replaced by gentle grinding using a glass rod in a 212 μm mesh sieve. The content of the 80-170 μm and 30-60 μm mesh sieves is separately dried at 40° C. and the dry material combined for polymer coating.

Example 2

Figures 4A, 4B:
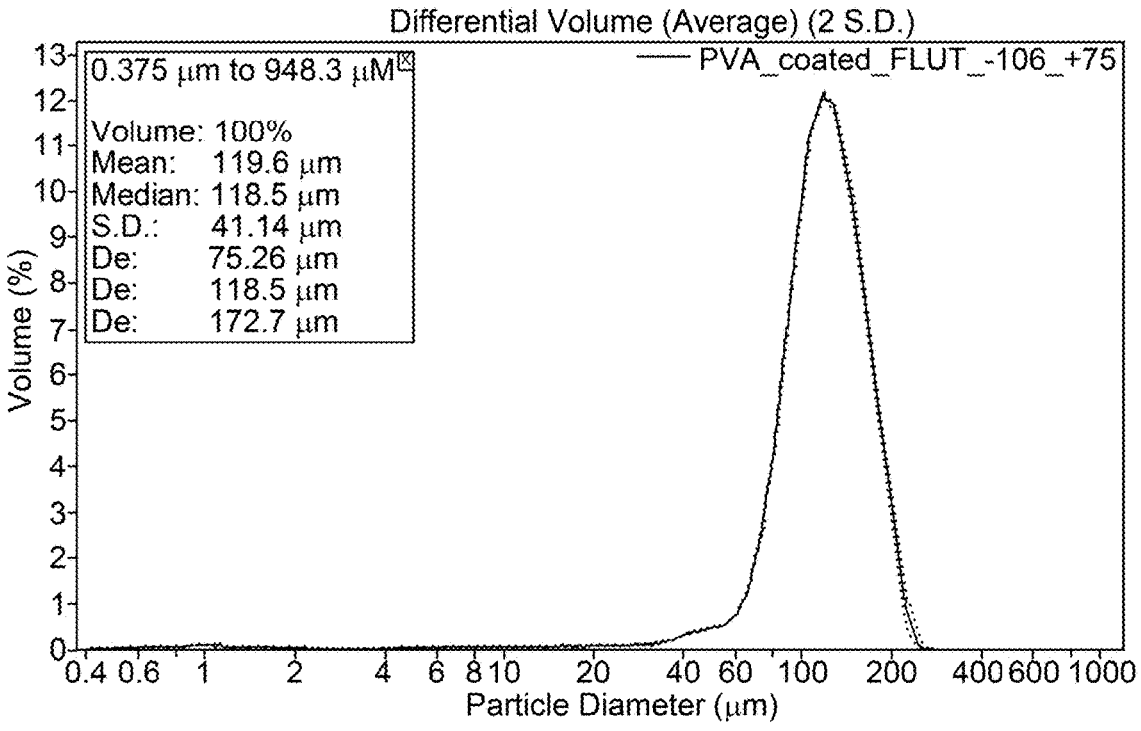
FIGS. 4A and 4B show the particle size distribution of the fluticasone propionate microparticles as compared to particle size distribution of triamcinolone hexacetonide (TA) (Kenalog™)

Size Distribution of Crystalline Drug Core 1 gram of fluticasone propionate (FP) powder (CAS 80474-14-2) was dissolved in 100 mL of ACS-grade methanol over a hot plate. The final solution was clear. This solution was cooled and allowed to rest for 24 h at room temperature. The resulting crystals were filtered, sieved and collected below 180 pm screens (~180 μm), cleaned with 0.1% TWEEN-80 aqueous solution, and washed twice with distilled water and dried at 40° C. for 3 h. 940 mg of fluticasone propionate crystals (94% yield) were obtained using this procedure. FIGS. 4A and 4B show the mean particle sizes obtained and size distributions.

FIG. 4A is a graph representing the particle size distribution of fluticasone propionate monodisperse distribution with mean particle size of ca. 110 μM, and the standard deviation is ca. 41 μM. Particles of these sizes can be injected easily through 23 g needle (internal diameter 320 μM)

As a comparison, FIG. 4B is a graph representing the particle size distribution of Traimcinolone Acetonide (Kenalog™). The mean particle size is ca. 20 μM. There is a relatively wide distribution with a second peak at ca. 1 μM. The standard deviation is about 13 μM. These small particles contribute to the burst effect seen with this type of formulation common in the prior art. See also FIG. 6.

Example 3

General Procedure for Coating Crystalline Drug Core

The dry FP crystals prepared according Example 1 are coated with polyvinyl alcohol (PVA, 2% w/v in 25% v/v isopropyl alcohol in DI-$H_2O$) in a model VFC-LAB Micro benchtop fluidized bed coater system (Vector Corporation) using the following range of parameters:

air flow, 50-60 L min$^{-1}$;
nozzle air, 5.0-25 psi;
pump speed, 10-35 rpm;
inlet temperature, 99° C.;
exhaust temperature, 35-40° C.;
spray on/off cycle: 0.1/0.3 min.

The PVA content is periodically measured by quantitative $^1$H nuclear magnetic resonance (NMR) spectroscopy by comparing the relative signal intensities of the FP and PVA resonances in the drug product to corresponding signals from calibration standards (See Example 3). A target final PVA concentration in the drug product is in the range of 0.1-20% w/w, or preferably 2-10% w/w. Coating of the particles is continued until the desired amount of PVA has been achieved. The coated particles are then dried in an oven at 40° C. for 1 h. The dry, coated particles are sieved in a sieve stack defined by 150 μm mesh and 53 μm mesh sieves.

Example 4

NMR Analysis for Determining Drug Content in Microparticles

NMR analysis was used to determine the amounts of the drug core and the polymeric shell in microparticles by calibrating with samples of known quantity of the pure drug.

Figure 5:
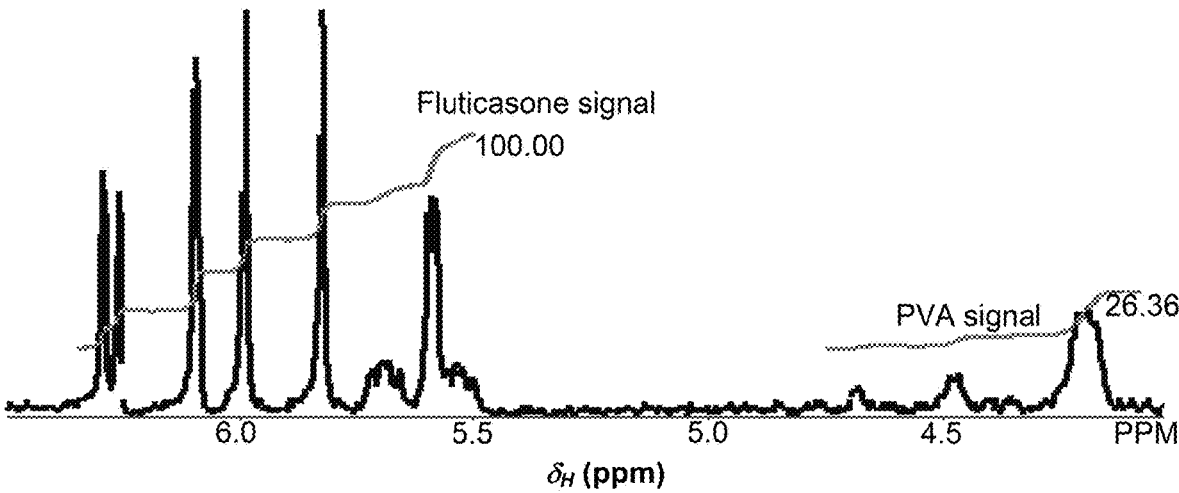
FIG. 5 is a graph showing the relative amounts of fluticasone propionate and PVA in microparticles by $^1$HNMR analysis.

The NMR system includes a Bruker Spectrospin 300 MHz magnet, Bruker B-ACS 120 autosampler, Bruker Avance II 300 console, and a Bruker BBO 300 MHz S1 5 mm with Z gradient probe. A calibration curve was prepared using five samples of known fluticasone propionate, and PVA concentrations made in NMR grade d6-DMSO. Proton (1H) NMR was run on two samples: the first containing only pure fluticasone propionate and the second containing PVA-coated fluticasone. Each sample was loaded manually and spun at 20 Hz inside the magnet. The probe was tuned and matched for proton (1H) NMR. The magnet was shimmed manually with the first sample in the magnet. Each sample was integrated for 1.5 hours with 1024 scans. Fluticasone peaks were integrated from 5.5 to 6.35 ppm, and the PVA peak was integrated from 4.15 to 4.7 ppm (see FIG. 5). Using this method, the finished coated fluticasone particles were determined to contain 2.1% PVA total weight of coated particles. Assuming spherical particle shape and mean particle diameter of 100 μm, this represents a coating thickness of ca. 7 μm.

Example 5

In Vitro Dissolution Analysis

To each vessel (1000 mL capacity) of a USP Type II dissolution system is added the dissolution medium and 3 mg of PVA-coated FP particles. The dissolution medium typically consists of 5-90% v/v of an alcohol-water mixture, where the alcohol can be methanol, ethanol, and isopropanol. The volume of dissolution medium used is in the 50-750 mL range. The temperature of the dissolution medium is maintained either at room temperature or at a temperature in the 5-45° C. range. Aliquots are removed from the dissolution medium at regular, predetermined time points and the samples are stored for subsequent analysis, such as with UV-visible absorption spectroscopy or high performance liquid chromatography.

A specific set of dissolution conditions is as follows:
drug for dissolution: 3 mg PVA-coated FP particles;
dissolution medium: 200 ml of 70% v/v ethanol and 30% v/v water;
dissolution temperature: 25° C.

Example 6

Thermal Processing and Effects on Dissolutions

The coated microparticles prepared according to Example 2 were thermal processed, i.e., heat treated for a specific period of time. Specifically, the interior of a borosilicate Petri dish was lined with aluminum foil and a monolayer of PVA-coated FP particles was spread. The dish was covered with perforated aluminum foil. An oven was pre-heated to the desired set-point and the samples were heat-treated for a pre-determined amount of time. The temperature set-point were 160° C., 190° C., 220° C. and 250° C.

FIG. 3A shows the dissolution profiles of microparticles having undergone heat treatments at the above temperatures. The dissolution conditions are as follows: 3 mg of PVA-coated FP microparticles were dissolved in a dissolution medium of 200 ml of 70% v/v ethanol and 30% v/v water at 25° C. The resulting concentration-time data are analyzed (e.g., one phase decay model) to afford the dissolution half-life (shown in FIG. 3B).

As shown in FIG. 3A, microparticles heat-treated at 220° C. have the slowest and gentlest initial release, as compared to those of microparticles treated at temperature above or below 220° C.

FIG. 3B shows that the dissolution half-lives of the microparticles of FIG. 3A. As shown, microparticles heat-treated at 220° C. have a significant longer dissolution half-life (12-20 hours) that those of the other microparticles (all less than 8 hours).

Example 7

Sustained Release (SR) Formulations for Animal Study (Sheep)

Dry FP crystals were prepared according to Example 1 and were coated with polyvinyl alcohol (PVA, 2% w/v in 25% v/v isopropyl alcohol in DI-$H_2O$) in a model VFC-LAB Micro bench top fluidized bed coater system (Vector Corporation) using the following range of parameters: air flow, 50-60 L/min; nozzle air, 23 psi; pump speed, 15 rpm; inlet temperature, 99° C.; exhaust temperature, 35-40° C.; spray on/off cycle: 0.1/0.3 min.

The resulting microparticles were then heat-treated at 130° C. for 3 hours.

The microparticles have mean diameters in the range of 60-150 μm. The PVA content of the resulting microparticles was 2.4% as analyzed by NMR analysis according to the method described in Example 4.

Example 8

Sustained Release (SR) Formulations for Animal Study (Dog)

Dry FP crystals were prepared according to the above procedures and were coated with polyvinyl alcohol (PVA, 2% w/v in 25% v/v isopropyl alcohol in DI-$H_2O$) in a model VFC-LAB Micro benchtop fluidized bed coater system (Vector Corporation) using the following range of parameters: air flow, 50-60 L/min; nozzle air, 8.0 psi; pump speed, 25 rpm; inlet temperature, 99° C.; exhaust temperature, 35-40° C.; spray on/off cycle: 0.1/0.3 min.

The resulting microparticles were then heat-treated at 220° C. for 1.5 hours.

The microparticles have mean diameters in the range of 60-150 μm. The PVA content of the resulting microparticles was 4.6% as analyzed by NMR analysis according to the method described in Example 4.

Figure 6:
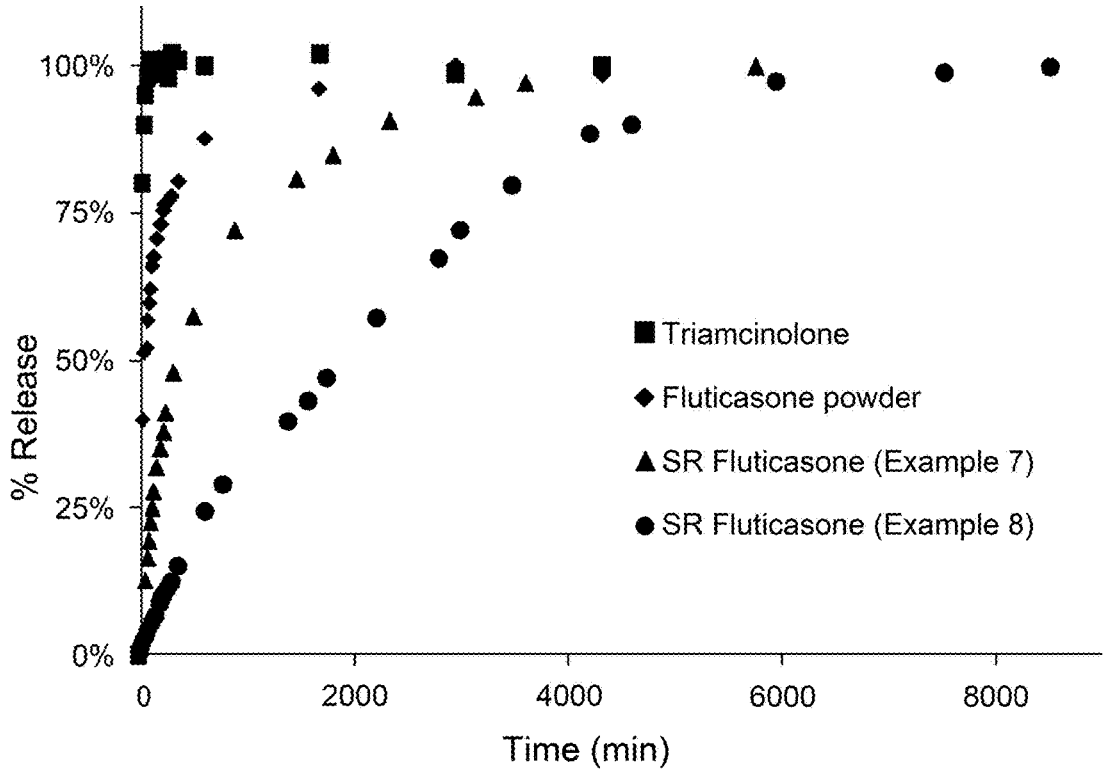
FIG. 6 is a graph showing dissolution profiles of triamcinolone hexacetonide (TA) as compared to sustained release (SR) formulations of fluticasone propionate (FP) according to embodiments of this disclosure.

FIG. 6 shows the dissolutions profiles of the microparticles prepared by Example 8 compared to the microparticles prepared by Example 7. In addition, FIG. 6 further shows the dissolution profiles of another corticosteroid (triamcinolone acetonide) and fluticasone propionate powder (uncoated, non-crystalline or very small, less than 10 μm crystals). Both coated FP microparticles (Examples 7 and 8) exhibit much longer dissolution half-lives and less initial bursts than the FP powder and triamcinolone acetonide. In addition, microparticles that have been heat-treated at 220° C. are shown to have even longer dissolution half-life than microparticles similarly prepared but heat-treated at 130° C. (Example 7).

The dissolution conditions were as follows:
drug for dissolution: 3 mg PVA-coated FP particles
dissolution medium: 200 ml of 70% v/v ethanol and 30% v/v water;
dissolution temperature: 25° C.

Example 9

Formulation of Suspension/Injectability

Optimized suspension formulations of coated particles were obtained using an iterative process, whereby different suspension solutions at varying concentrations were assessed for their ability to keep coated particles in suspension. The most homogeneously distributed formulations were then injected through needle sizes ranging from 18 to 25 gauge. Particle transfer efficiency was measured by HPLC. A 1% CMC solution provided the maximum suspension and a 23 gauge needle provided adequate injection efficiency.

Sterility. Polymer-coated fluticasone particles were steam-sterilized (122° C., 16 psi, 30 min) in amber vials. The sterilization process did not affect the chemical composition of the formulation according to 1H NMR spectroscopy and HPLC analysis. See FIG. 5. In vitro studies in 500 mL USP Type II systems confirmed that the sterile material had the same fluticasone release profile as the same material prior to autoclaving.

Example 10

In Vivo Pharmacokinetic (Pk) Studies (Sheep)

In a non-GLP exploratory study, the local toxicity and drug concentration levels were evaluated for 3 months in sheep (n=4) after a single intra-articular injection into the left stifle joint using a 23G needle of a tuberculin syringe. The injectable dosage form was 0.5 mL of 20 mg extended release fluticasone propionate (EP-104) prepared according to Example 7.

Clinical observations were performed throughout the study, and histopathology was performed at the end of the study to evaluate local toxicity. To evaluate fluticasone propionate concentration levels in treated knees, synovial fluid samples were collected at designated time points. Blood was collected throughout the study to determine plasma concentration levels. Plasma fluticasone levels were measured by HPLC-MS. Mistry N, et al. Characterisation of impurities in bulk drug batches of fluticasone propionate using directly coupled HPLC-NMR spectroscopy and HPLC-MS. *Journal of Pharmaceutical and Biomedical Analysis* 16(4):697-705, 1997. Mortality, morbidity, and body weights were also evaluated.

There were no changes during clinical observations, and no histopathologic changes occurred in any of the knees after 3 months. There was no mortality or morbidity, and sheep gained weight throughout the study.

Fluticasone propionate concentrations were detected in synovial fluid at 3 months (n=4; 11.51, 9.39, 13.22, and 18.89 ng/mL). Plasma concentration levels were less and declined at a greater rate than those of synovial fluid Fluticasone propionate concentrations in plasma were below quantifiable limits (BQL) at 0 or below 0.3 ng/mL beginning at Day 70. Plasma and synovial fluid concentrations throughout the study are provided in FIG. 7.

Of note is an absence of burst and sustained local concentrations achieved for the duration of the experiment. The reported EC50 for fluticasone propionate is 7-30 pg/ml. Möllmann H, et al. Pharmacokinetic and pharmacodynamic evaluation of fluticasone propionate after inhaled administration, *European journal of clinical pharmacology* February; 53(6):459-67, 1998. Significantly, after 90 days, the local concentration of FP in the synovial fluid remained considerable amount (n=4; 11.51, 9.39, 13.22, and 18.89 ng/mL) and above the EC50 level, while the plasma concentration was no longer detectable (the plasma concentration became BQL at day 70).

Figure 7:
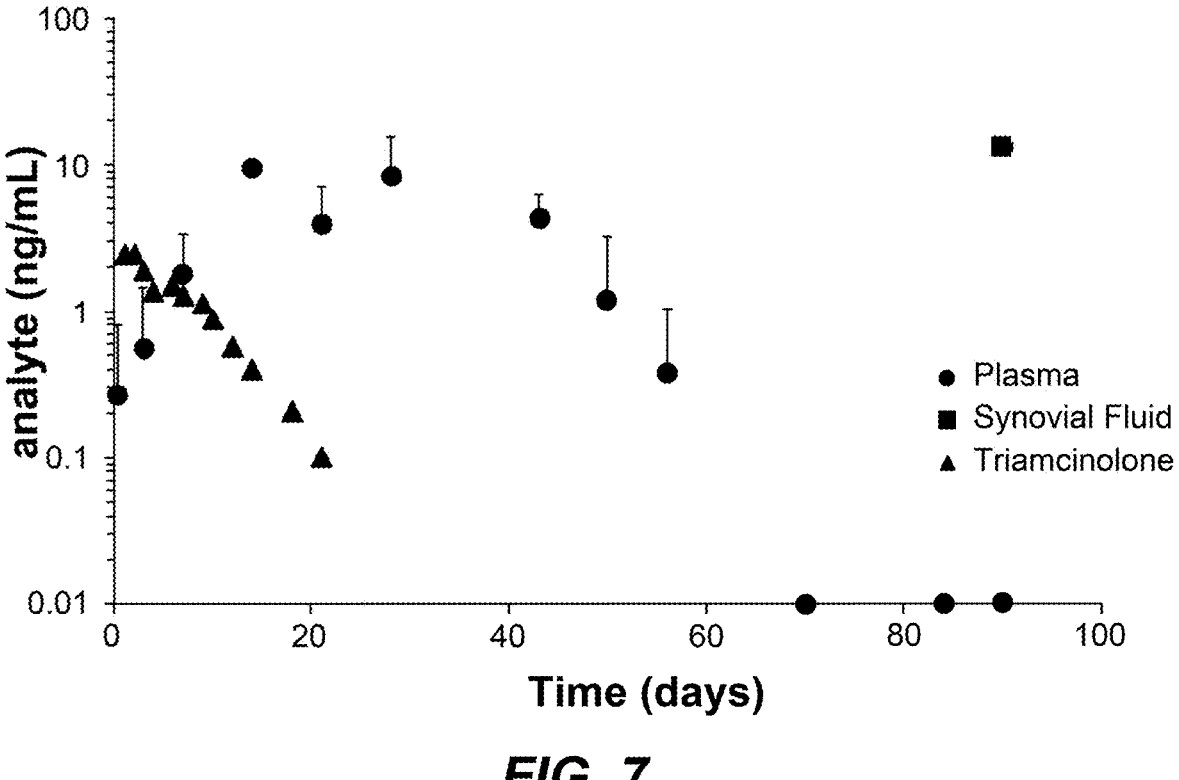
FIG. 7 is a graph showing plasma fluticasone (FP) levels, synovial fluid FP levels after injection of 20 mg formulation into knee joint of sheep as compared to intra-articular pharmacokinetics of triamcinolone hexacetonide (40 mg) from human subjects.

As a comparison, the release of triamcinolone hexacetonide (40 mg) from human subjects is also plotted in FIG. 7. Derendorf H, et al. Pharmacokinetics and pharmacodynamics of glucocorticoid suspensions after intra-articular administration. *Clinical Pharmacology and Therapeutics* March; 39(3):313-7 (1986). As shown, triamcinolone hexacetonide release shows a significant initial burst followed by rapid decline. The duration of release is significant shorter than that of the coated FP microparticles described herein, despite having a much higher initial dose.

The shape of the PK curve of the corticosteroid microparticles is substantially different from that of the triamcinolone hexacetonide. The slow rise and near constant release over a period of 60 days confirms the release mechanism of pseudo-zero order, by which the corticosteroid drug is released at a nearly constant rate so long as a saturated solution can be maintained within the polymeric shell (e.g., for 60 days), irrespective of the original drug loading.

Figure 8A:
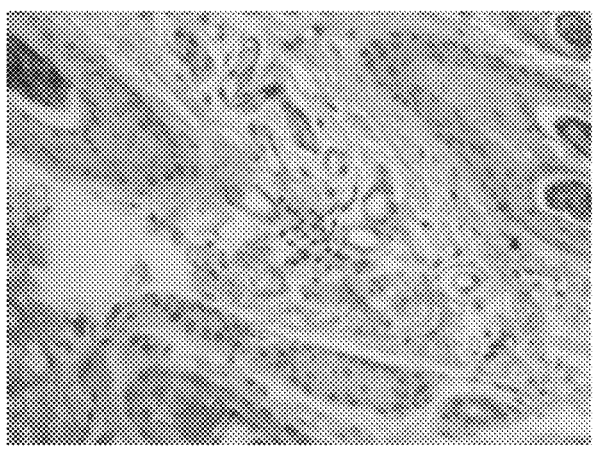
FIGS. 8A, 8B and 8C demonstrate the results of a histological examination of the injected joints of sheep showing no abnormalities.
Figure 8B:
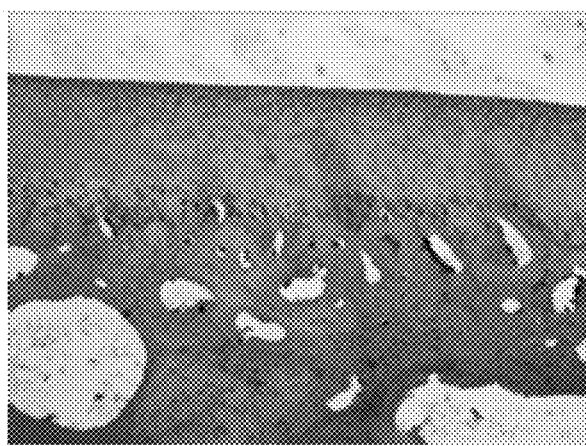
Figure 8C:
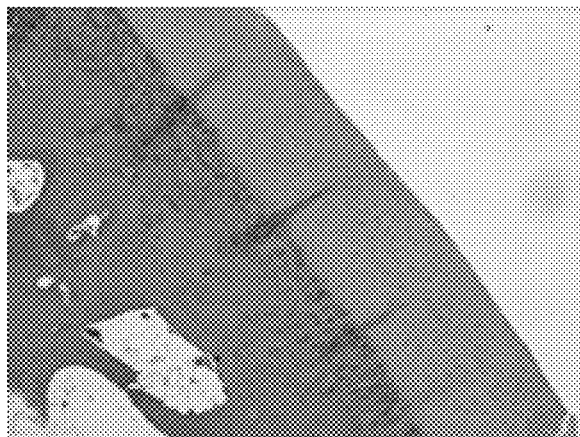

The animals were euthanized on day 90 and the joints excised and sent for histology. There were no safety or toxicity issues noted on clinical examination. Histological examination of the injected joints showed no abnormalities (FIGS. 8A, 8B, and 8C).

Example 11

In Vivo Pharmacokinetic (Pk) Studies (Dogs)

Extended release fluticasone propionate formulation (EP-104IAR) was prepared according to Example 8. The in vivo release characteristics were evaluated in the knee of Beagle dogs (n=32) during a 60-day study. Two groups of 16 male and female dogs were evaluated. Group 1 (n=8 males and 8 females) were administered a target dose of 0.6 mg EP-104IAR by intra-articular injection (the low dose group). Group 2 was administered a target dose of 12 mg EP-104IAR by intra-articular injection (the high dose group).

Synovial fluid and plasma were collected at 7, 29, 46, and 60 days after injection, and cartilage tissue drug concentrations and microscopic changes were also evaluated at these time points. Mortality checks, clinical observations, and body weight measurements were performed. Blood was collected for plasma bioanalysis from all surviving animals at pre-dose, and on Days 3, 5, and 7; and twice weekly thereafter until necropsy (including the day of necropsy).

Two animals/sex from each group were euthanized on Day 7, 29, 46 or 60. Prior to necropsy, synovial fluid was collected for bioanalysis.

Figure 9:
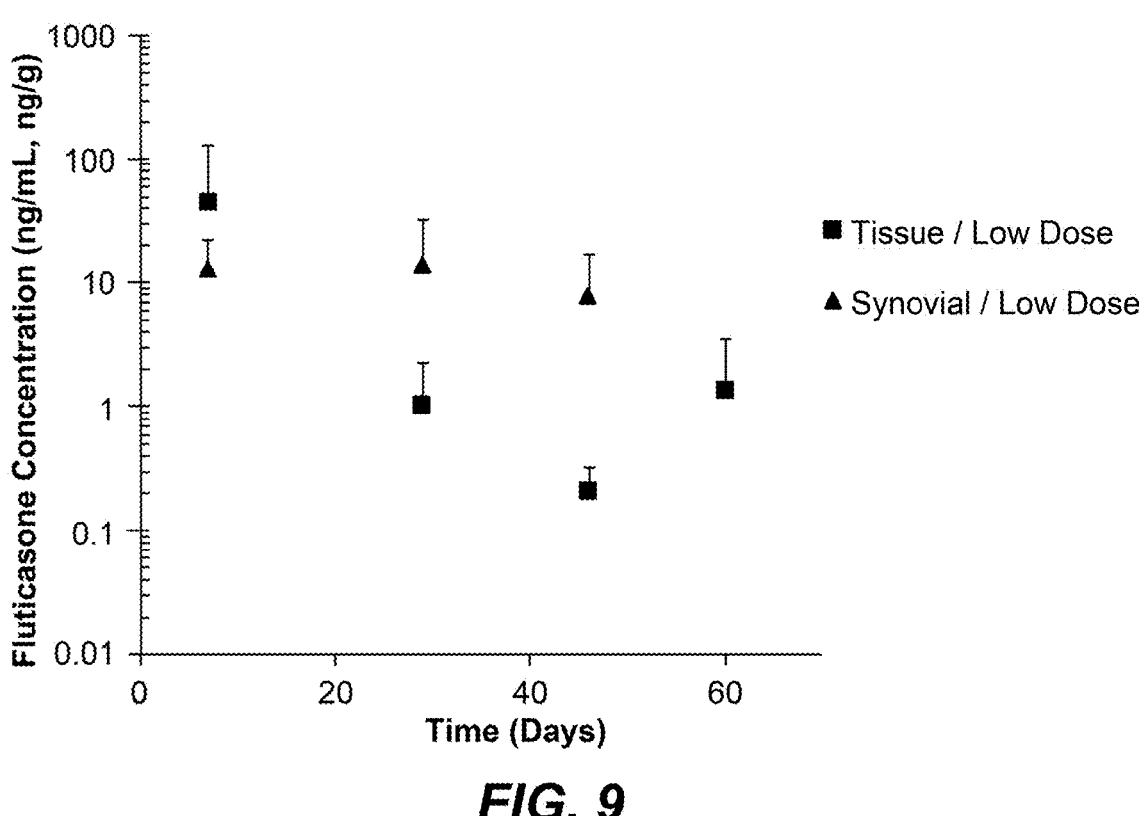
FIG. 9 shows the local concentrations in tissue and synovial fluid of knee joints of dogs for a period of 60 days following a single injection of a low dose fluticasone propionate. The plasma concentrations were too low to detect.

Results:

In the low dose group, there were no measurable concentrations of free fluticasone propionate in plasma at any of the sampling time points, indicating the drug remained in the joint. See FIG. 9.

In the high dose group, measurable but low plasma concentrations occurred on Day 3 after injection and ranged from 0.2 to 0.5 ng/mL. On the other hand, local concentrations of the drug in the synovial fluid and tissue were significantly higher throughout the entire period of the study. See FIG. 10.

Figure 10:
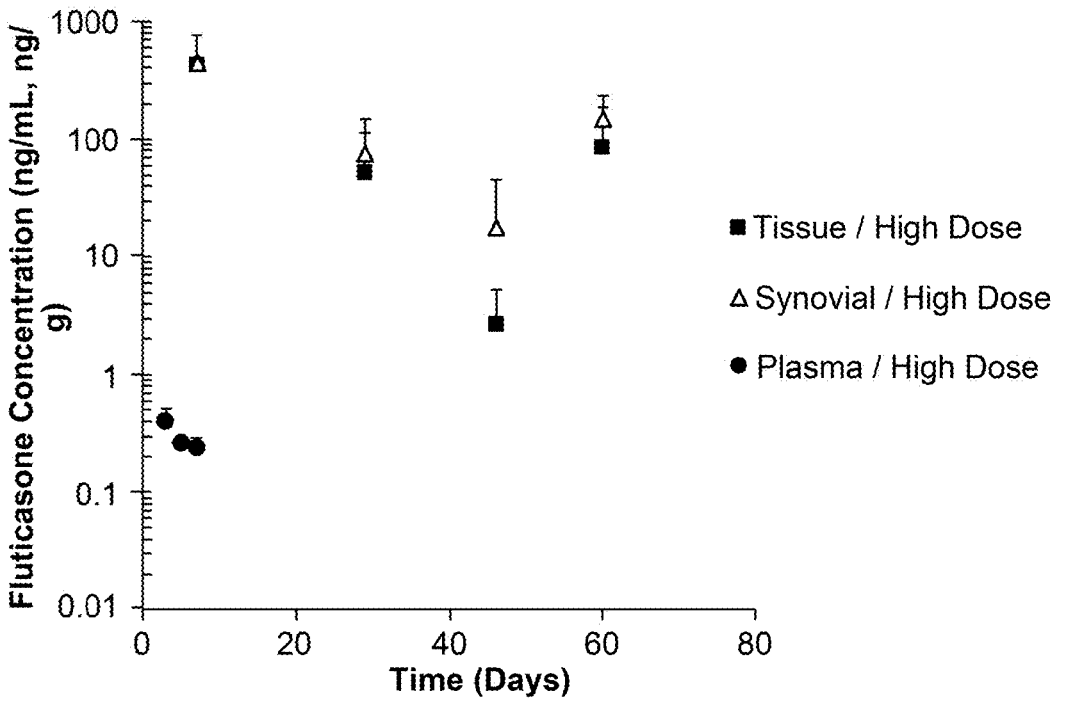
FIG. 10 shows the local concentrations in tissue and synovial fluid of knee joints of dogs, as well as the plasma concentrations, for a period of 60 days following a single injection of a high dose fluticasone propionate.

The highest concentrations of fluticasone propionate in synovial fluid generally occurred on Day 7 in both dose groups and ranged from 3 to 25 ng/mL in the low dose group (FIG. 9) and 179 to 855 ng/mL in the high dose group (FIG. 10). In the low dose group, measurable fluticasone propionate concentrations in synovial fluid were detected at Day 60, but concentrations were below the limit of quantification (1.0 ng/mL) at this collection time point. Fluticasone propionate concentrations in synovial fluid of high dose animals at Day 60 were 97 to 209 ng/m L.

Example 12

Comparative Results—Sheep Vs. Dog Studies

FIG. 6 demonstrates the impact on dissolution characteristics by a thermal processing step during the microparticle formation. In particular, microparticles that have undergone a precision thermal processing step (220° C. for 1.5 hours) exhibited a significantly longer dissolution half-life than that of microparticles that have undergone a thermal processing step at a much lower temperature (130° C. for 3 hours). The result indicates that the precision thermal processing step at 220° C. has caused certain structural changes in the polymeric shell that in turn altered its permeation characteristics.

Microparticles that have undergone different thermal processing steps were used in the sheep study (heat-treated at 130° C.) and dog study (heat-treated at 220° C.) and their in vivo sustained release behaviors were discussed in Examples 9 and 10, respectively.

Figure 11:
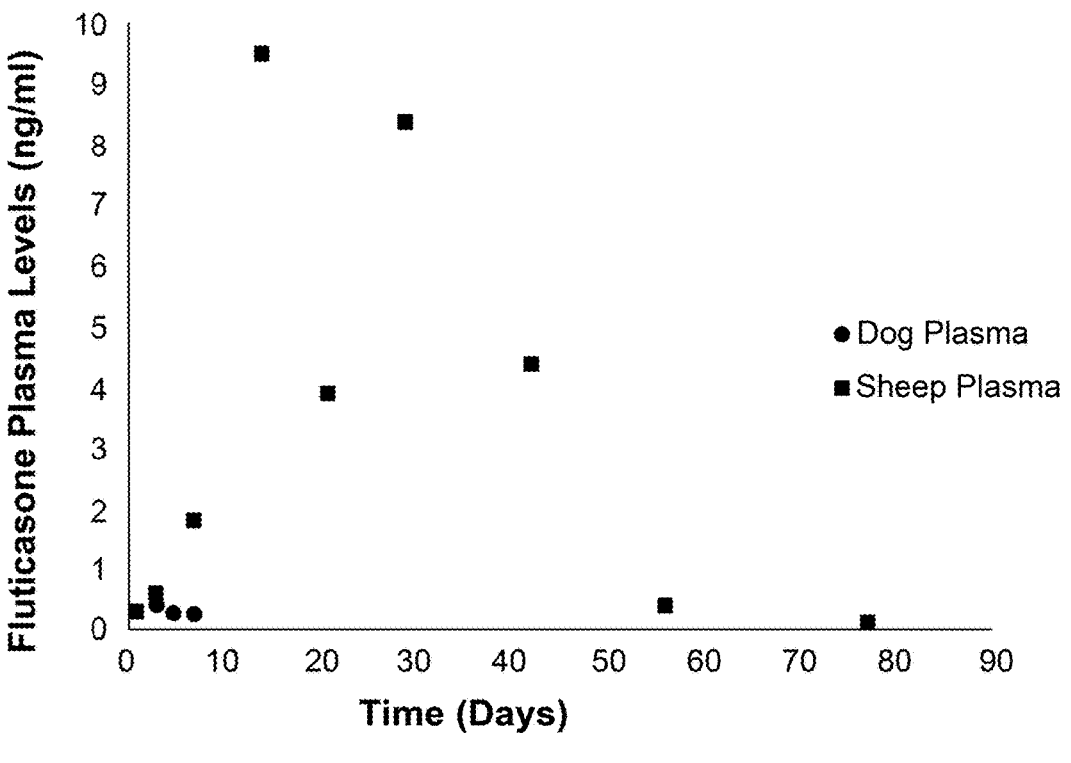
FIG. 11 shows the plasma concentrations of fluticasone propionate following injections to the knee joints of sheep as compared to those of dogs. The microparticles for each injection had undergone different heat-treatments prior to being formulated into injectable compositions.

FIG. 11 shows the plasma concentrations measured in the sheep study as compared to those in the dog study. As shown, the plasma concentrations in the sheep study exhibited much higher concentrations after 3 days, when compared to those in the dog study, despite the fact that the sheep received a substantially lower dose (0.25 mg/kg) than the dogs (1.2 mg/kg). Moreover, the plasma concentrations in the dogs were largely constant before they became undetectable. In contrast, the plasma concentrations in the sheep exhibited more variations over the release period. The results indicate that the thermal processing step during the microparticle formation had a significantly impact on the release behaviors in vivo, much like it did on the dissolution behaviors in vitro (See Example 8).

Example 13

Lack of Initial Burst

Fluticasone propionate microparticles were prepared according to Example 8. Microparticles having mean diameters in the range of 50-100 μm were used to study the plasma pharmacokinetic (PK) in the first two days following injection. Two groups of dogs (n=3 per group) were injected with a 2 mg dose (low dose) and a 60 mg dose (high dose), respectively.

Figure 12:
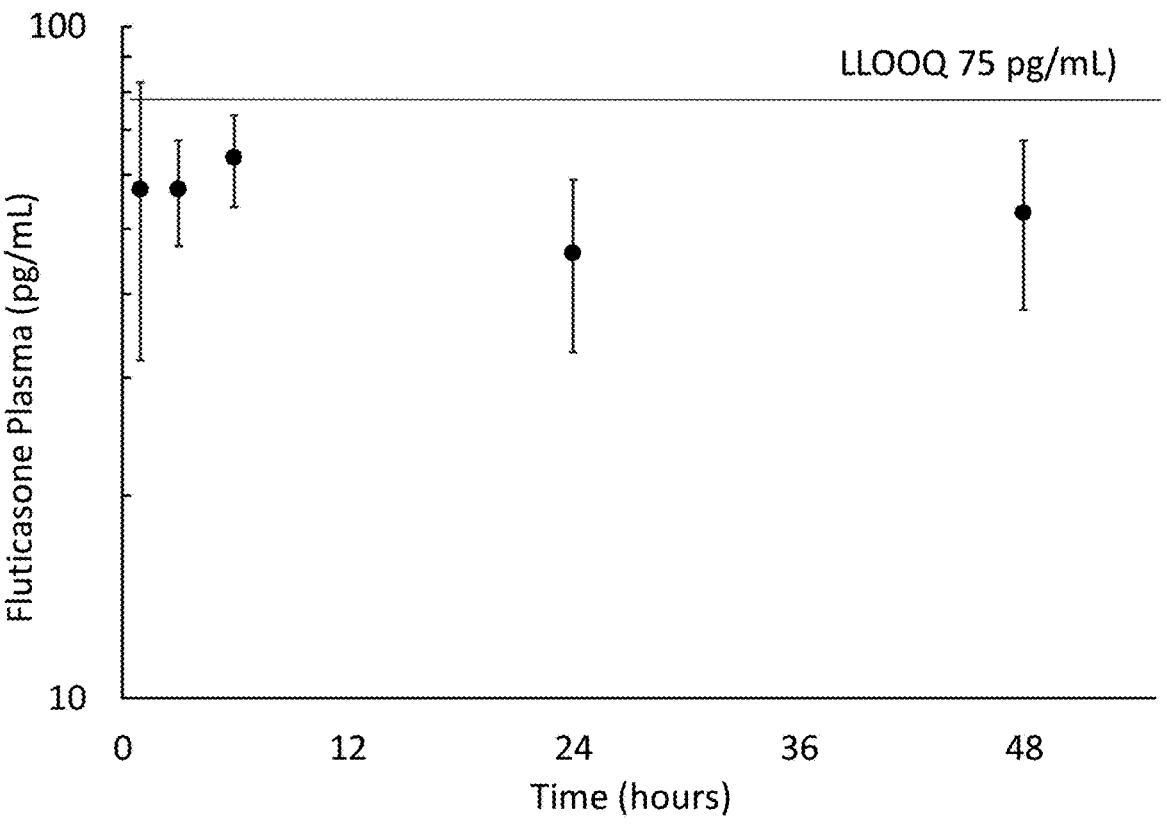
FIG. 12 shows the plasma concentrations of fluticasone propionate in the knee joints of dogs over a period of 45 hours following a single injection. The pharmacokinetic (PK) curve indicates a lack of initial burst.

Most sustained release formulations are expected to exhibit an initial burst or a peak in the plasma within the first 48 hours following dosing. Unexpectedly, however, the FP sustained release formation according to an embodiment of this disclosure shows no initial burst. FIG. 12 shows a complete absence of initial burst or peak in the first 2 days in the high dose group and all samples were below limit of quantification (albeit detectable). In the low dose group only a single sample was detectable, but was below quantification. Accordingly, the sustained release formulations described herein are capable of highly localized delivery of a corticosteroid (e.g., fluticasone propionate) while keeping the systemic corticosteroid below the level that may result in any clinically significant HPA axis suppression. Significantly, the complete absence of an initial burst in even the high dose group indicates that the in vivo release is following a zero-order or pseudo-zero order pattern.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

We claim:

1. A unit dosage form comprising:
   a plurality of microparticles, each microparticle including:
   (1) a crystalline drug core of more than 70% by weight of the microparticle; and
   (2) a polymeric shell encapsulating the crystalline drug core,
   wherein the crystalline drug core consists of one or more crystals of a corticosteroid selected from fluticasone, fluticasone furoate, and fluticasone propionate, and the polymeric shell is polyvinyl alcohol (PVA) and is in contact but immiscible with the crystalline drug core;
   wherein the plurality of microparticles have a mean diameter in the range of 50 μm to 150 μm and a standard deviation of less than 50% of the mean diameter; and
   wherein the plurality of microparticles are heat-treated at 210-230° C. for at least one hour and the unit dosage form releases the corticosteroid over a period of 2-12 months while maintaining a minimum therapeutically effective concentration of the corticosteroid within a body compartment.

2. The unit dosage form according to claim 1, wherein the body compartment is a joint, an epidural space, an intravitreal space, a surgically created space, or a space adjacent to an implant.

3. The unit dosage form according to claim 1, wherein, within the sustained release period of 2-12 months, the corticosteroid is released locally within the body compartment and provides below a quantifiable limit of plasma corticosteroid 7 days after injection.

4. The unit dosage form according to claim 1, wherein each microparticle of the plurality of microparticles comprises 90-98% w/w of crystalline drug core and 2-10% w/w of polymeric shell.

5. An extended release formulation comprising a plurality of microparticles having a core/shell morphology and been heat-treated at 210-230° C. for at least one hour, wherein each microparticle includes: (1) a crystalline drug core of more than 70% by weight of the microparticle, wherein the crystalline drug core consists of one or more crystals of fluticasone, a salt or ester thereof; and (2) a polymeric shell encapsulating the crystalline drug core, whereby the polymeric shell is PVA and is in contact but immiscible with the crystalline drug core, wherein said plurality of microparticles have a mean diameter of between 80 μm and 150 μm.

6. The extended release formulation according to claim 5, wherein the fluticasone, salt or ester thereof is selected from fluticasone, fluticasone furoate, and fluticasone propionate.

\* \* \* \* \*